US012588849B2

(12) United States Patent
Nasry

(10) Patent No.: US 12,588,849 B2
(45) Date of Patent: Mar. 31, 2026

(54) GARMENT MEDICAL EXAMINATION SYSTEM

(71) Applicant: Samer Nasry, Franklin, MI (US)

(72) Inventor: Samer Nasry, Franklin, MI (US)

(73) Assignee: Scientific American Medical Examination Research, LLC, Franklin, MI (US)

( * ) Notice: Subject to any disclaimer, the term of this patent is extended or adjusted under 35 U.S.C. 154(b) by 331 days.

(21) Appl. No.: 18/446,628

(22) Filed: Aug. 9, 2023

(65) Prior Publication Data

US 2024/0050010 A1    Feb. 15, 2024

Related U.S. Application Data

(60) Provisional application No. 63/396,483, filed on Aug. 9, 2022.

(51) Int. Cl.
| | |
|---|---|
| *A61B 5/256* | (2021.01) |
| *A61B 5/00* | (2006.01) |
| *A61B 5/0205* | (2006.01) |
| *A61B 5/282* | (2021.01) |
| *A61B 1/05* | (2006.01) |
| *A61B 5/022* | (2006.01) |

(52) U.S. Cl.
CPC ............ *A61B 5/256* (2021.01); *A61B 5/0053* (2013.01); *A61B 5/0205* (2013.01); *A61B 5/282* (2021.01); *A61B 5/6806* (2013.01); *A61B 1/05* (2013.01); *A61B 5/02233* (2013.01)

(58) Field of Classification Search
CPC ..... A61B 5/256; A61B 5/0053; A61B 5/0205; A61B 5/282; A61B 5/6806; A61B 1/05; A61B 5/02233; A61B 7/003; A61B 7/02
See application file for complete search history.

(56) References Cited

U.S. PATENT DOCUMENTS

| | | | |
|---|---|---|---|
| 6,425,862 | B1 | 7/2002 | Brown |
| 7,156,808 | B2 | 1/2007 | Quy |
| 7,249,036 | B2 | 7/2007 | Bayne |
| | | (Continued) | |

FOREIGN PATENT DOCUMENTS

| | | | | |
|---|---|---|---|---|
| CN | 108888260 A | * | 11/2018 | ............. A61B 5/318 |
| CN | 211511859 U | | 9/2020 | |
| | | (Continued) | | |

*Primary Examiner* — Michael J Lau

(74) *Attorney, Agent, or Firm* — Young Basile Hanlon & MacFarlane, P.C.

(57) ABSTRACT

A glove that includes a set of electrocardiogram leads coupled to the glove and configured to record a 12-lead electrocardiogram by contacting a body of a user with the set of electrocardiogram leads. The set of electrocardiogram leads include precordial leads that contact a chest of the user and are positioned along a peripheral edge of the glove that connects a palmar side of the glove to a dorsal side of the glove. The set of electrocardiogram leads also includes a first arm lead that is configured to contact a first arm of the user and is positioned on the palmar side of the glove spaced apart from the peripheral edge. Additionally, the set of electrocardiogram leads includes a second arm lead that is configured to contact a second arm of the user and is positioned on the dorsal side of the glove spaced apart from the peripheral edge.

20 Claims, 12 Drawing Sheets

(56) References Cited

U.S. PATENT DOCUMENTS

| | | | | |
|---|---|---|---|---|
| 8,442,615 B2* | 5/2013 | David | ..................... | A61B 5/341 |
| | | | | 600/387 |
| 9,208,288 B2 | 12/2015 | Putrino | | |
| 9,872,628 B2 | 1/2018 | Hyde et al. | | |
| 11,786,161 B2* | 10/2023 | Nasry | ..................... | A61B 5/316 |
| | | | | 600/324 |
| 2001/0000526 A1 | 4/2001 | Gopinathan et al. | | |
| 2002/0045805 A1* | 4/2002 | Gopinathan | ......... | A61B 5/6806 |
| | | | | 128/903 |
| 2002/0111777 A1 | 8/2002 | David | | |
| 2009/0171166 A1 | 7/2009 | Amundson et al. | | |
| 2013/0172691 A1 | 7/2013 | Tran | | |
| 2013/0267818 A1 | 10/2013 | David et al. | | |
| 2014/0143064 A1 | 5/2014 | Tran | | |
| 2016/0256104 A1 | 9/2016 | Romem et al. | | |
| 2016/0360965 A1 | 12/2016 | Tran | | |
| 2017/0000369 A1* | 1/2017 | Hyde | ..................... | A61B 5/6806 |
| 2017/0000370 A1* | 1/2017 | Hyde | ..................... | G16H 15/00 |
| 2017/0270331 A1* | 9/2017 | Hoeink | ................ | G06Q 10/087 |
| 2017/0354373 A1* | 12/2017 | Kostic | ................... | A61B 5/282 |
| 2018/0132815 A1 | 5/2018 | Tsai et al. | | |
| 2019/0231262 A1* | 8/2019 | Nasry | ..................... | G16H 80/00 |
| 2021/0045683 A1* | 2/2021 | Nasry | ..................... | H04R 3/005 |
| 2021/0081042 A1* | 3/2021 | Baier | ..................... | G06F 3/014 |
| 2022/0104721 A1* | 4/2022 | Nasry | ................. | A61B 5/6826 |
| 2023/0139248 A1* | 5/2023 | Ravuri | ................ | A61B 5/6826 |
| | | | | 600/301 |
| 2024/0050010 A1* | 2/2024 | Nasry | ................. | A61B 5/0205 |

FOREIGN PATENT DOCUMENTS

| | | | |
|---|---|---|---|
| EP | 2744403 A1 | 6/2014 | |
| EP | 3202320 A1 | 8/2017 | |

* cited by examiner

GARMENT MEDICAL EXAMINATION SYSTEM

CROSS-REFERENCE TO RELATED APPLICATIONS

This application claims priority to and the benefit of U.S. Provisional Application Ser. No. 63/396,483, filed Aug. 9, 2022, the entire disclosure of which is incorporated by reference herein.

FIELD

The present teachings generally relate to devices and systems for performing physical medical examinations, and more particularly, to wearable garments and an associated system that measures and monitors vital signs to treat various health conditions.

BACKGROUND

An increased cost of healthcare coupled with increases in population and patient age have led to significant developments in remote medical treatment devices. These remote medical devices help facilitate medical treatment of patients who can or do not physically travel to a medical office or hospital. As a result, more patients, such as those incapacitated or house-ridden, are able to receive more thorough medical care, resulting in various health conditions being detected and treated at an earlier stage—prior to the health condition reaching a point where hospitalization is necessary.

These remote medical treatment devices may often involve a transmission of medical records (i.e., past medical history, allergies, medications) along with patient medical data from a patient location to a central medical facility. The central medical facility may then evaluate the records and data to determine if any health condition is present in the patient that requires treatment. After evaluation, the central medical facility may communicate with the patient any treatment plan or further steps needed.

However, remote medical treatment devices are often inaccurate or over-simplified for patient use. As a result, the medical data transmitted to the central medical facility may be significantly limited or incorrect, resulting in frequent misdiagnosing of health conditions or inadvertently overlooking a health concern of a patient. Furthermore, because the remote medical treatment devices may be rather limited in functionality, medical professionals may be hesitant to offer remote communication or still require a patient to physically visit a medical office, even after remote data collection.

There remains a need for a medical device system that accurately records and transmits medical data from a patient to an external location. What is needed is a medical device system that includes one or more wearable garments having a plurality of sensors that accurately receive data from a patient and transmit that data to an external location. Additionally, there remains a need for a medical device system easy and simple enough for a patient to operate independently of a medical professional. What is needed is a medical device system that includes one or more wearable garments that track patient data in a streamlined fashion. Moreover, there remains a need for a medical device system that robustly collects a plurality of vitals from a patient to accurately evaluate the data for any potential health concerns. Thus, what is needed is a medical device system having a plurality of interconnected sensors and devices that detect and record extensive vitals of a patient. Additionally, there remains a need for a medical device system that remotely and accurately records heart and lung auscultation of a patient.

SUMMARY

One aspect of the present disclosure is a glove that includes a set of electrocardiogram leads coupled to the glove and configured to record a 12-lead electrocardiogram by contacting a body of a user with the set of electrocardiogram leads. The set of electrocardiogram leads include precordial leads that are configured to contact a chest of the user and are positioned along a peripheral edge of the glove that connects a palmar side of the glove to a dorsal side of the glove. The set of electrocardiogram leads also includes a first arm lead that is configured to contact a first arm of the user and is positioned on an interior surface of the palmar side or the dorsal side of the glove spaced apart from the peripheral edge. Additionally, the set of electrocardiogram leads includes a second arm lead that is configured to contact a second arm of the user and is positioned on the dorsal side of the glove spaced apart from the peripheral edge.

Another aspect of the present disclosure is a glove that includes a set of electrocardiogram leads coupled to the glove and configured to record an electrocardiogram of a user, a tapping mechanism, a pulse oximeter located on a first finger of the glove, a camera located on a second finger of the glove, and a blood pressure cuff coupled to a wrist portion of the glove and located adjacent to the tapping mechanism. The set of electrocardiogram leads includes three or six precordial leads that extend along a peripheral edge of the glove that connects a palmar side of the glove to a dorsal side of the glove, a right arm lead positioned on the wrist portion of the glove in a liner of the glove on the palmar side of the glove, and a left arm lead positioned on an outer surface of the dorsal side of the glove that is configured to contact the left arm of the user when the glove is worn on the right hand of the user. The right arm lead is configured to contact a right arm of the user when the glove is worn on a right hand of the user. Additionally, the tapping mechanism includes a housing coupled to the wrist portion of the glove, a motor disposed in the housing, and an arm in communication with the motor. The motor articulates the arm to generate a tapping movement that is configured to contact the body of the user.

Moreover, the present teachings meet one or more of the present needs by providing: a medical device system that accurately records and transmits medical data from a patient to an external location; a medical device system that includes one or more wearable garments having a plurality of sensors that accurately receive data from a patient and transmit that data to an external location; a medical device system easy and simple enough for a patient to operate independently of a medical professional; a medical device system that includes one or more wearable garments that track patient data in a streamlined fashion; for a medical device system that tracks robustly collects a plurality of vitals from a patient to accurately evaluate the data for any potential health concerns; a medical device system having a plurality of interconnected sensors and devices that detect and record extensive vitals of a patient; a medical device system that remotely and accurately records heart and lung auscultation of a patient; or a combination thereof.

DETAILED DESCRIPTION

Figure 1:
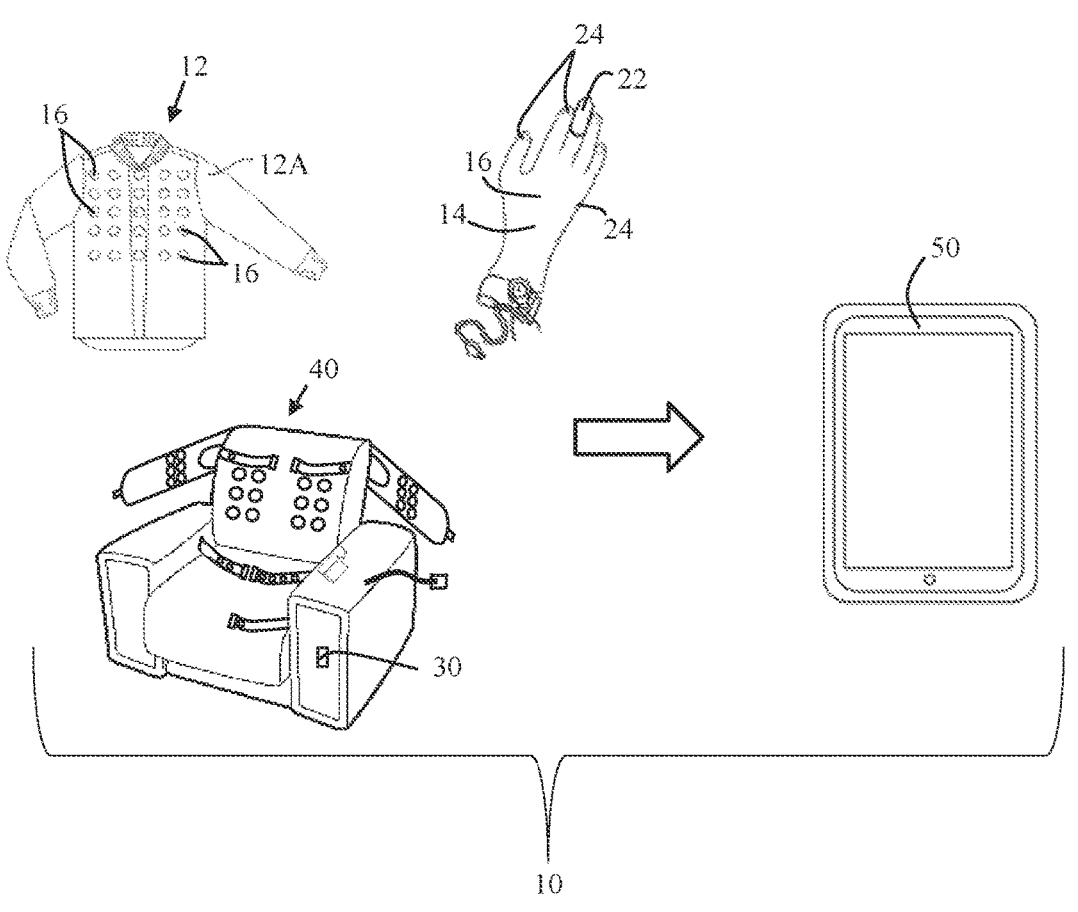
FIG. 1 is a perspective view of a medical device system.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the description herein, but should instead be determined with reference to the appended claims, along with the full scope of equivalents to which such claims are entitled. The disclosures of all articles and references, including patent applications and publications, are incorporated by reference herein in their entirety for all purposes. Other combinations are also possible as will be gleaned from the following claims, which are also hereby incorporated by reference in their entirety into this written description.

The present teachings generally relate to a medical device system. The medical device system may function to identify, measure, or both an extensive range of vital and physical examination signs of a patient for remote medical care. It is envisioned that the medical device system described herein provides medical professionals and patients alike the ability to record data based upon a specific patient in order to properly evaluate a variety of health conditions without requiring a patient to be physically present in a medical facility. For example, the medical device system may be utilized for patients that are incapacitated or otherwise unable to travel to a medical facility, such as a hospital or a physician's office, to evaluate potential health risks while the patient remains a home—all without jeopardizing the level of healthcare expected when a patient enters an actual medical facility. Additionally, it is envisioned that the medical device system may facilitate healthcare of patients remotely without exposing those patients to potential health risks in a medical facility, such as those present during a pandemic.

The medical device system may include a number of devices interconnected to form the system. The medical device system may include one or more wearable components, one or more accessories, one or more electronic devices, or a combination thereof. Advantageously, all or only a portion of the devices within the medical device system may be utilized for a specific application. For example, all devices may be utilized to compile data based on a patient more at risk of health complications while minor evaluations may only utilize a single device within the medical device system. Thus, it may be gleaned from the present teachings that the medical device system is highly customizable and portable for a number of different remote applications.

The medical device system may include a garment. The garment may function to provide at least a partial medical evaluation of a patient by recording, tracking, or otherwise collecting key medical data. The garment may then transfer such data offsite from a patient's location (e.g., the patient's home) to an offsite physician, to a computer-based medical system, or the like. The garment described herein may be utilized by any patient desiring examination and treatment for most medical conditions while remaining in the comfort of their own home. The patient self-testing using the garment may conduct as thorough, or even more thorough, an analysis than an in-office doctor visit. The results of the self-exam may be easily transmitted to the home medical software or a medical professional where it can be determined if further tests are required, a prescription is required, a specialist is required, if immediate medical attention is necessary, or a combination thereof. The garment may be similar to those described in U.S. patent application Ser. No. 16/265,339, all of which is incorporated herein for all purposes.

The garment may be shaped as a jacket, a vest, a wrap, a poncho, or the like. The garment may include a plurality of electrocardiogram leads, a plurality of auscultation acoustic sensor devices located in one or more of an anterior chest wall, posterior chest wall, anterior abdominal section, posterior abdominal section, or any combination thereof to provide optimal heart and lungs auscultation, a flexible respiratory sensor, one or more cuff portions (e.g., blood pressure cuff portions) located on an at least one arm portion of the garment, and a hardware device for sending and receiving signals via wired or wireless communication. The garment may include a section that contacts a patient's abdomen. The garment may include a section that contacts a patient's lower back. The garment may include a plurality of devices that are removably connected to or work in tandem with the garment. These devices may include but are not limited to: a pulse oximeter, otoscope, oralscope, ophthalmoscope, PanScope, and oral temperature device.

The garment may include a plurality of auscultation acoustic sensor devices or other microphones anywhere along the garment. The microphones may collect data from a patient by recording sound coming from one or more internal organs of the patient. The microphones may be strategically arranged in a manner which forms a blanket that hugs the patient thorax providing optimal heart and lungs auscultation. The auscultation acoustic sensor devices (e.g. microphones; stethoscopes) may be utilized to record one or more of a patient's lung sounds including but not limited to clear breathing sounds, reduced breathing sounds, diffuse wheezing, basilar crackles, and scattered rhonchi, or absence of breathing sounds. The auscultation acoustic sensor devices (e.g. microphones, stethoscopes, or the like) may be utilized to record one or more of a patient's heart and lung sounds including but not limited to: normal heart sounds; S1 heart sound; S2 heart sound; murmurs; aortic stenosis; mitral regurgitation; pulmonic stenosis; aortic insufficiency, any other heart valve and/or heart muscle disease, any other lung disease, or a combination thereof. The auscultation acoustic sensor devices may provide a description of the location, strength, type, and quality of the recorded sound. The auscultation acoustic sensor devices may be individually numbered in the garment to aid in determining the location of the lung and heart sounds. Thus, the acoustic sensors or microphones may be site specific such that each recorded sound may be pinpointed back to a specific microphone along the garment.

The microphones may be positioned anywhere along the garment. The microphones may be located on a front portion of the garment that contacts a chest of the patient. The microphones may also be located on one or more sides of the garment located along a ribcage of the patient. Additionally, the microphones may be positioned along a back side of the garment adjacent to the patient's back. Thus, it is envisioned that the microphones may be highly customizable and tunable based on the desired recordings needed. Additionally, the microphones may be removable for easy replacement if damaged, further modification, or both.

The microphones may include a rubber ear. The rubber ear may encompass all or a portion of the microphones. The rubber ear may function to funnel sound more accurately from a patient into the microphone for accurate recordings. The rubber ears may contact a patient's body and protect the microphone from direct contact with a patient. Thus, the rubber ears may ensure a longer life for each microphone without needing frequent replacement. Additionally, the rubber ears may be flexible or rigid. However, it is envisioned that the rubbers ears may be flexible to at least partially form a patient's body contour, thereby creating a better funnel and seal for directing a sound from the patient's organs into the microphone. Furthermore, the microphones may be configured to function as a digital stethoscope, whereby the microphones may include a diaphragm that may be configured to at least in part detect and/or facilitate detection of a sound from a user's or patient's body.

It is contemplated that the garment and microphones may be high portable. As such, the garment may be free of any external wires and may not require and power source to conduct testing on a patient. Therefore, the garment may include one or more power sources, such as a battery or other power source to power the microphones along the garment. The battery may be any battery, such as a lithium ion battery, that may be secured along or within the garment. For example, the battery may be stitched into one or more layers of the garment in a manner that does not obstruct the accurate recordings of the microphones. The battery may be rechargeable, replaceable, or both without damaging the garment. The battery may include a port to connect a cord purely for recharging purposes. Therefore, the garment may advantageously be used a number of times for remote patients regardless of where the patient is located.

By providing a substantially self-sufficient medical testing garment, the garment may record a desired number of data points for further evaluation and analysis. The data points may be collected from the plurality of microphones and then compiled to create a final report. The data compiled may be transmitted (via one or more transmitters of the garment) to a computing device. The computing device may perform one or more processes and/or manipulations on the data received from the garment before outputting a report or final analysis. For example, the data may be initially filtered to remove any unwanted "white noise" present when collecting the data. Additionally, the data may also be amplified to a desired sound level before compiling and interpreting the data.

As one non-limiting example, data from a plurality of microphones may undergo filtering, buffering, and/or amplifying of the soundwaves to produce a signal. The signal may then be converted from analog format to digital format. The signal may then be filtered. The signal may then be normalized. At that point, the normalized signal may be analyzed and transmitted. It should be noted that any one or more of the above processes may be completed in the garment itself, in the external computing device or both. Once the normalized signal is established, the data may be fully analyzed and/or output in a final report, thereby providing a medical professional succinct data to evaluate a patient's current condition.

The garment may be adapted for transmitting data (e.g., through a wired or wireless connection). The data may be collected and may optionally be stored on a hardware device associated with the garment which may be a computing device, or which may transfer data to a computing device. Any of the detection devices described herein (the stethoscope, the microphone, the electrocardiogram leads, the probe, the pulse oximeter, otoscope, oralscope, ophthalmoscope, PanScope, oral temperature device) may facilitate collection of data and may be adapted to transmit the data to a hardware associated with the garment. Alternatively, any of the detection devices described herein may be adapted to transmit data directly to a computing device.

The devices associated with the garment may be embedded in the garment or removably attached to the garment. The devices may be located into pockets formed on the garment. The devices may be fastened to the garment by one or more of a strap, a hook, a snap, a flexible band, or any mechanical fastening device.

The medical device system may also include a glove. The glove may function to provide a medical evaluation and/or examination of a patient by recording, tracking, or otherwise collecting key medical data. A full and complete medical evaluation and/or examination may be completed by the glove to determine potential health issues and/or risks of the patient. The glove may then transfer such data offsite from a patient's location (e.g., the patient's home) to an offsite physician or the like. The glove may be utilized by any patient desiring examination and treatment for a number of medical conditions while remaining in their own home. For example, the glove may be used during a pandemic where travelling to a medical facility poses a health threat to the patient. The glove may be delivered to the patient first to conduct an initial examination and gather vitals or other critical data from the patient. Based upon the data collected from the glove, the medical professional may then determine if further evaluation is needed using or if the patient is not at risk and requires no further examination.

The glove may include a plurality of electrocardiogram (EKG) leads. Advantageously, the glove my conduct a 12-lead EKG by positioning the glove directly on the patient in one or more positions to collect enough data from the leads to create a full 12-lead EKG report for a medical professional. It should also be noted that while a 12-lead EKG is discussed herein in further detail, any number of EKG leads may be incorporated. For example, the glove may include more than 12 EKG leads or less than 12 EKG leads. Additionally, each EKG lead may be positioned and recorded a single time during an EKG test, or one or more of the EKG leads may be positioned and recorded multiple times. As a result, the glove may provide significant flex-ibility in developing a robust and accurate EKG of a patient by recording any number of leads.

The electrocardiogram leads may be integrated into the glove or may be located onto a separate substrate that is secured to the glove when worn by a patient. For most accurate results, the electrocardiogram leads may make direct contact with the patient's skin free of any conven-tional adhesives, thereby allowing the electrocardiogram leads to be used for numerous tests. The electrocardiogram leads may be positioned anywhere along the glove. For example, the electrocardiogram leads may be positioned in different configurations based on the size, height, weight, etc. of a patient conducting the self-exam. While either a left-handed glove or a right-handed glove may be utilized based on the teachings herein, it is envisioned that a right-handed glove may provide a patient the greatest flexibility to accurately contact their chest and conduct a proper EKG. Specifically, because the heart is located on the left side of the chest cavity, a right-handed glove will allow a patient to conduct a proper EKG more easily with a larger range or motion.

The electrocardiogram leads may be positioned along a peripheral edge of the gloves, one or more fingertips of the glove, a central portion of the glove, or a combination thereof. The electrocardiogram leads may be located on the backside (e.g., dorsal side) of the glove, the inside palm portion (e.g., palmar side) of the glove, or both. The elec-trocardiogram leads may include precordial electrocardio-gram leads, a left arm lead, a right arm lead, left leg lead, right leg lead, or a combination thereof (e.g., V1-V6). The electrocardiogram leads may be used to record data that may facilitate calculations of the aVF, aVL, aVR, or a combina-tion thereof. Thus, the glove may be positioned along the user's chest, sternum, or both to gather data for each required electrocardiogram lead, thereby allowing a com-puting device to calculate and compile an overall EKG. It should be noted that the glove may include a battery or power source to facilitate recording and transmitting the data from the electrocardiogram leads or other devices.

Advantageously, unlike a conventional EKG requiring adhesively attached leads secured to a patient's skin, the electrocardiogram leads of the glove may require no adhe-sive and may be moved along a patient's skin with ease. Furthermore, the electrocardiogram leads may wirelessly transmit data to a computing device, thereby improving the transportability of the glove when compared to a conventional EKG device. As a result of the wireless transmittal, the glove may be positioned anywhere along a patient's body that is reachable by the patient themselves. The glove may be positioned horizontally along the chest and/or sternum of the patient, vertically along the chest and/or sternum of the patient, or anywhere in between. Additionally, spacing may be established by the patient wearing the glove such that the electrocardiogram leads are spaced apart a sufficient dis-tance for accurate data measurements. For example, the electrocardiogram leads may be located on various fingertips so that fingers may be spaced apart and pressed against the patient's skin for measurement. The distance between the electrocardiogram leads may depend on the patient, but the angle formed between the electrocardiogram leads on fin-gers of the gloves may be about 45 degrees or more, about 90 degrees or more, or about 135 degrees or more. The distance may be about 180 degrees or less, about 160 degrees or less, or about 140 degrees or less. As discussed above, the positioning of the electrocardiogram leads may be adjusted to most accurately record all electrocardiogram leads and accurately record a proper EKG. Thus, the elec-trocardiogram leads may be positioned and/or repositioned one or more times to accurately record the electrocardio-gram lead readings. For example, the aVL and aVR elec-trocardiogram leads may be recorded substantially simulta-neously by positioning both leads on the patient, or alternatively, the aVL and AVR may be recorded separately by positioning each lead individually. As such, it may be gleaned that the glove allows for great customization and flexibility when recording data from electrocardiogram leads.

The glove may also include one or more additional devices. For example, the glove may include a blood pres-sure cuff to measure blood pressure, a pulse oximeter to measure blood oxygen saturation, a microphone similar to those of the garment, or a combination thereof. The micro-phone may be positioned along the patient to record sounds from one or more positions, thereby allowing patients to conduct full cardiopulmonary auscultation in the same man-ner a physician would conduct heart and lung auscultation. For example, the microphone of the glove may be positioned along an upper portion of the chest over the heart, a lower portion of the chest over the heart, along a patient over one or more both lungs, or a combination thereof. Similarly, the microphone (e.g., a digital stethoscope) may be positioned on chest and back concurrently to imitate similar recording provided when a patient were to use a vest as described herein.

The glove may also include one or more position location sensors. The position location sensors may determine a position of the glove along a patient's body. As a result, data can be accurately recorded and correlated to a specific location without manually dictating a proper location. Addi-tionally, it is envisioned that the position location sensors may be used to establish initial testing parameters for the glove. For example, the position location sensors may be moved around a perimeter of a testing area to provide a baseline of where the glove is in relationship to one or more organs of the patient (e.g., the heart, the lungs, etc.). By establishing a baseline, all subsequent testing conducted using the stethoscope, one or more EKG leads, or a com-bination thereof may be accurately correlated to a specific location within the boundaries of the perimeter initially established. Additionally, it may then be possible to deter-mine any "outlies" during testing for any recorded locations that do not fall within the specific boundaries.

Thus, based on the above, the electrocardiogram leads may collect data in conjunction with the one or more additional devices (e.g., the microphone) to complete a full EKG workup on a patient. It should be noted that the data collected from the glove may be transmitted in a similar manner as the data collected from the garment. For example, the data may be transmitted and thereafter augmented, organized, or manipulated (i.e., filtered, amplified, or both) before outputting an organized data report for a medical professional to evaluate.

The medical device system may include a club designed primarily for abdomen examination. The club may function to provide at least a partial medical evaluation of a patient by recording, tracking, or otherwise collecting key medical data. The club may then transfer such data offsite from a patient's location (e.g., the patient's home) to an offsite physician or the like. The club described herein may be utilized by any patient desiring examination and treatment for most medical conditions while remaining in the comfort of their own home.

The club may be used to provide separate and independent testing of a patient by conducting an abdomen exam on the patient. The club may be used in addition to the garment, the glove, the chair, or a combination thereof to conduct such abdomen exams. For example, the club may include a microphone (e.g., a digital stethoscope) to record sounds within a specific location on the patient's body. Additionally, the club may include a position location sensor to determine a specific location where data is being recorded.

It is envisioned that the club may be used to determine specific locations of pain along a patient's body. To do so, the club may include a mechanism that applies pressure or otherwise contacts the patient. When a patient feels discomfort in a specific location, the club may then record a location for further evaluation by a medical professional. To further determine the severity of any discomfort, the club may also include one or more pressure sensors to more accurately record how much pressure is applied to an area of discomfort, thereby even further allowing accurate analysis of a patient's health concerns.

In addition to locations of pain, the club may also search for tenderness along a patient's body, such as in their head, chest, back, limbs, abdomen, or a combination thereof. To determine such tenderness, the club may include a mechanism that contacts the patient's skin and delivers a percussion into the patient's body. That percussion may then be evaluated and interpreted for tympanicity or dullness. Additionally, the club may check for rebound tenderness by exhibiting a sudden release of a contact point using a quick-release mechanism.

To allow for such percussion, the club may include a structure that "taps" the patient's skin and creates that percussion. The structure may include a rotary mechanism, spring, actuator, motor, gears, or a combination thereof that actuates one or more tapping mechanisms. The structure may be manually or electrically operation. The mechanism may be battery operated. The structure may be any mechanism that allows for a "tapping" motion to be delivered to a patient.

The contact by the structure may be done by one or more small arms that act as a tapping mechanism. The tapping mechanisms may extend from the rotary mechanism, actuator, motor, gears, or the like and may be actuated by the rotary mechanism, actuator, motor, gears, or the like. The tapping mechanisms may extend in any desired direction. In addition to the tapping mechanisms, the club may include one or more devices, such as a microphone, sensor, or both. Thus, it is envisioned that the club may receive the reflected sound waves created by tapping after striking the abdomen internal organs or masses, thus creating an ultrasound-like picture and/or sound that can detect organomegaly, the presence of mases, or both. As a result, the tapping mechanisms may create the percussion and a patient may provide an input on the trigger or other input device to indicate pain in a given position.

The medical device system may also include a chair. The chair may function to provide at least a partial medical evaluation of a patient by recording, tracking, or otherwise collecting key medical data. The chair may then transfer such data offsite from a patient's location (e.g., the patient's home) to an offsite physician or the like. The chair described herein may be utilized by any patient desiring examination and treatment for most medical conditions while remaining in the comfort of their own home.

The chair may be used in conjunction with, or in lieu of, the glove, the garment, or both to perform a self-evaluation on a patient. Thus, the chair may include one or more devices similar to the glove, the garment, or both. For example, the chair may include one or more microphones similar to those of the garment and the glove. However, the chair may also include one or more additional devices different than the glove and the garment. It should be noted that the devices of the chair may be powered by a power source within the chair, such as a battery.

The chair may include one or more straps. The straps may function to at least partially encompass a patient seated in the chair. The straps may be secured around at least a portion of the patient, such as their chest, torso, abdomen, or a combination thereof. The straps may be outfitted with electrocardiogram leads, microphones, other devices, or a combination thereof. Each strap may include a variety of devices or may be designed for one particular type of testing. For example, a first set of straps may include electrocardiogram leads to conduct a proper EKG of a patient while a second set of straps may include one or more microphones to detect and/or record sounds from within the patient. It should be noted that the straps may be used simultaneously or may be used sequentially.

The straps may be any flexible material that may follow a contour or a patient's body. The straps may be a fabric, plastic, or both. The straps may include one or more fasteners, clips, buckles, or a combination thereof to secure the straps to each other, to the chair, or both. The straps may be located anywhere along the chair to properly contact a patient in a desired location. The straps may also include armholes to further facilitate close contact with the body of a patient, thereby allow the patient to at least partially "wear" the straps during testing, as further described herein.

The chair may also include one or more additional devices. The additional devices may include one or more pressure sensors. The pressure sensors may detect the presence of a patient sitting in the chair. The pressure sensors may detect a weight or locally applied force by a patient. The pressure sensors may provide an initial signal to begin testing. For example, the pressure sensors may be located along the chair to ensure a proper posture of the patient prior to conducting a self-examination. Thus, the pressure sensors may be located on a seat of the chair, a back of the chair, or both.

The chair may include one or more microphones embedded directly within a back of the chair, a wearable garment connected to the chair, or both. The microphones may be the same or different to those within the glove, the garment, or both. The microphones may be location specific to determine where specific recording occur. The microphones may be flexible, such as by utilizing a rubber ear, to follow a contour of a patient's body.

The chair may also include one or more air compartments. The air compartments may fill with air to identify locations of pain and/or discomfort of a patient sitting in the chair. The air compartments may be any desired size and/or shape. The air compartments may be positioned anywhere along the chair to strategically contact desired portions of the patient's body. The air compartments may be controlled by the patient in the chair or may be remotely controlled via the computing device or other external remote by a medical professional.

The computing devices and/or the data gathered by the one or more devices with the medical device system may be accessible by one or more of a physician office (e.g., a physician, a physician's assistant, a nurse practitioner, a nurse, a medical resident, a medical assistant, a medical billing associate, or other medical office staff), a pharmacy, a caretaker, a family member, an emergency medical treatment professional, an insurance company, or any individual who may take an action based upon the data. The office and/or individual receiving the data is then able to make medical diagnosis decisions based upon the data. It is possible that the computing device may also replace the human doctor as it may be programmed so that it can establish a diagnosis, recommend testing, and/or prescribe medications.

The computing device may receive data from the medical device system (i.e., the chair, the glove, the garment, or a combination thereof), transmit data to the medical device system, or both. Thus, the computing device may have a receiver, a transmitter, or both in communication with the rest of the medical device system to create two-way communication, three-way communication, or even four-way communication. The computing device may be located anywhere in wireless connection with the medical device system. Thus, the computing device may communicate with the devices of the medical device system via wireless connection such as Bluetooth. However, the computing device may also communicate using the internet (e.g., wi-fi) or a corded connection. It should be noted that the computing device may be any electronic device, such as a table, mobile phone, computer, etc.

Turning now to the figures, FIG. 1 illustrates a perspective view of a medical device system 10. The medical device system 10 includes a garment 12, a glove 14, a chair 40, or a combination thereof in communication with a computing device 50. The garment 12 includes a plurality of microphones 16 that are configured to detect and record sound from a user's heart, lungs, or both. It is envisioned that the user wears the garment similar to a conventional jacket such that the plurality of microphones 16 are located along a user's body adjacent to the user's heart, lungs, or both to record sounds emanating from the heart, lungs, or both. As a result, the plurality of microphones 16 may create a sound pulmogram, a sound cardiogram, or both that is communicated from the garment 12 to the computing device 50.

The medical device system 10 may also include a glove 14 to record one or more vitals of a user. For example, as illustrated in FIG. 1, the glove 14 may include a pulse oximeter 22 that records a user's oxygen saturation. The oxygen saturation levels may then be communicated from the glove 14 to the computing device 50. Additionally, as further described below, the glove 14 may include a microphone 16, such as a digital stethoscope, and one or more electrocardiogram leads 24 to complete a full EKG, complete accurate auscultation of the hearts and/or lungs, or both by moving the glove 14 to one or more desired positions anywhere along the patient. For example, the glove 14 may record heart and lung sounds via the microphone 16 in one or more predetermined locations. The predetermined locations may be determined by an associated medical software system instructing examination using the glove 14. Similarly, the glove 14 may also include a position location sensor (see FIG. 4) that may track a position of the glove 14 while the microphone 16 of the glove 14 creates a comprehensive sound map when the patient moves the glove 14 along their chest to one or more locations.

Furthermore, the vitals data recorded, such as the oxygen saturation level of a user or auscultation results, may then be transmitted directly to the computing device 50 or may pass through one or more manipulation steps to organize or modify the data prior to transmitting the data to the computing device 50. As a result, the data may be interpretated by a medical professional after being received by the computing device 50.

Additionally, the medical device system 10 may include a chair 40. A user may be seated in the chair 40 in an upright position so that the chair 40 may collect a variety of vitals or other data from a user and transmit such data to the computing device 50 via a transmitter 30 located along the chair 40 to help diagnose potential health conditions. To collect the user data and help diagnose health conditions, the chair 40 may include one or more microphones to record sound from the user's body, one or more air compartments 36 to determine potential pain locations along a user's body, or both. Additionally, the chair 40 may include one or more pressure sensors to determine a user's weight, to determine when a user is present in the chair 40, or both.

For example, a user may sit in the chair 40 so that the pressure sensors sense a presence of the user. The pressure sensors may be in different locations along the chair 40 to ensure a desired posture of the user. One configuration may include a first pressure sensor located on a seat of the chair 40 and a second pressure sensor located on a back of the chair 40. Accordingly, the chair 40 may detect that a user is properly seated in the chair 40 with their back against the back of the chair 40. However, it should be noted that the pressure sensors located along the chair 40 may be positioned in any desired location to sense a positioning and/or posture of a user. Additionally, the chair 40 may be configured remotely from the computing device 50 (or any other external device) by receiving a command and/or signal via a receiver 28 of the chair 40. Further details and configurations of the chair 40 are discussed below to describe the chair 40 shown in FIG. 7.

It is envisioned that that garment 12, the glove 14, and the chair 40 may each be utilized individually as a sole device for a patient to measure and record vitals or other data based upon the patient's body. The recorded data may then be processed or otherwise manipulated to evaluate the health of the patient. As such, it should be noted that the garment 12, the glove 14, or both may also include one or more transmitters 30, one or more receivers 28, or both to communicate with the computing device 50 so that the recorded data from the garment 12, the glove 14, or both is transmitted to the computing device 50 for further analysis. Beneficially, the computing device 50 may be located near the devices 12, 14, and 40, or may be located at an offsite location such that a patient may conduct their testing using the medical device system 10 free of physical interaction with a medical professional. Additionally, the medical device system 10 may allow for a patient who may otherwise be unable to easily reach a medical facility gain proper medical care. For example, during a pandemic, a patient may easily gain medical care via the medical device system 10 without a need to enter a medical facility and risk exposure to a health threat.

The computing device 50 may also include a transmitter, a receiver, or both that communicate with the garment 12, the glove 14, the chair 40, or a combination thereof. Thus, the computing device 50 may wirelessly, or via one or more cables, transmit data to and from the garment 12, the glove 14, the chair 40, or a combination thereof. As a result, a medical professional may receive the data from the devices 12, 14, and 40 on the computing device 50 to help diagnose a potential medical condition of the patient. Additionally, due to two-way communication between the computing device 50 and the other devices 12, 14, and 40, the computing device 50 may also send various data and/or commands to the devices 12, 14, and 40. For example, the computing device 50 may send a signal to initiate operation of the devices 12, 14, and 40, change settings or configurations of the devices 12, 14, and 40, or both.

Figure 2:
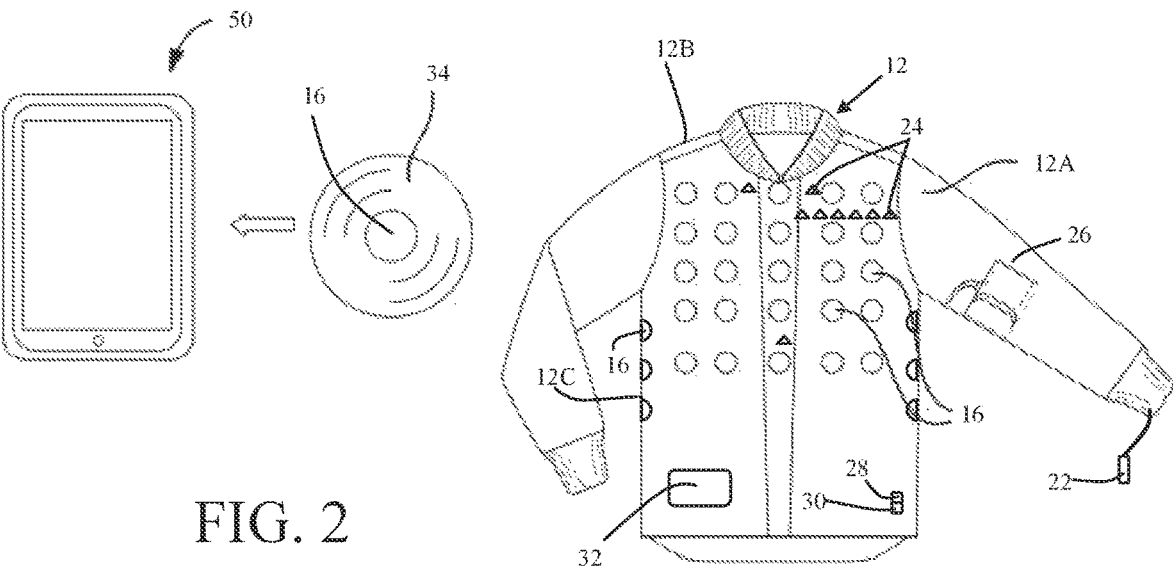
FIG. 2 is a perspective of a garment having a plurality of microphones.

FIG. 2 illustrates a perspective view of a garment 12 in accordance with the present teachings. The garment 12 may include a plurality of microphones 16 distributed along one or more sides of the garment 12. For example, as illustrated, the microphones 16 may be located on a front of the garment 12A, one or more sides of the garment 12C, a back of the garment 12B, or a combination thereof. It is envisioned that the microphones 16 may be site specific such that, when the garment 12 is worn by a patient, the microphones 16 align with one or more organs of the patient. For example, at least a portion of the microphones 16 may align with the lungs of the patient, the heart of the patient, or both to detect and/or record a sound emitted from the lungs, the heart, or both to analyze the auscultation thereof. Due to a plurality of microphones 16 being utilized to track the sound of the organs, the garment 12 may advantageously compile a plurality of sounds from various positions to create a sound pulmogram, a sound cardiogram, or both. The microphones 16 may be positioned to at least partially surround the one or more of the organs (such as the lungs and/or heart) such that converging data taken from the microphones 16 creates an accurate sound pulmogram, a sound cardiogram, or both.

Furthermore, the garment 12 may include one or more electrocardiogram leads 24 to complete a full EKG of a patient. It is envisioned that the electrocardiogram leads 24 may complete a full 12-lead EKG. However, the garment 12 may beneficially allow for additional electrocardiogram leads 24 to receive further data points. For example, the electrocardiogram leads 24 may be located on both a front side of the garment 12 aligned with the chest of a patient and the back side of the garment 12 aligned with the back of a patient. Thus, the electrocardiogram leads 24 may receive surface electrical signals from both sides of the heart. It should also be noted that one or more microphones 16 may be located on the back side of the garment 12 as well as the front side.

Each microphone 16 may be surrounded by a rubber ear 34 to more accurate funnel sound from the patient into the microphone 16. Additionally, the garment 12 may beneficially include a battery 32 or other power source located within the garment 12 to power the microphones 16 or one or more additional items, such as a pulse oximeter 22 connected to a sleeve of the garment 12, a blood pressure cuff 26 integrated into a sleeve of the garment 12, or both. Thus, the garment 12 may be used by a patient without being constrained by one or more power cords or other tethers, thereby making the garment 12 significantly transportable. Furthermore, the garment 12 may beneficially communicate with a computing device 50 via a transmitter 30, a receiver 28, or both to send and/or receive data from the computing device 50, thereby further optimizing remote operation of the garment 12.

Figure 3:
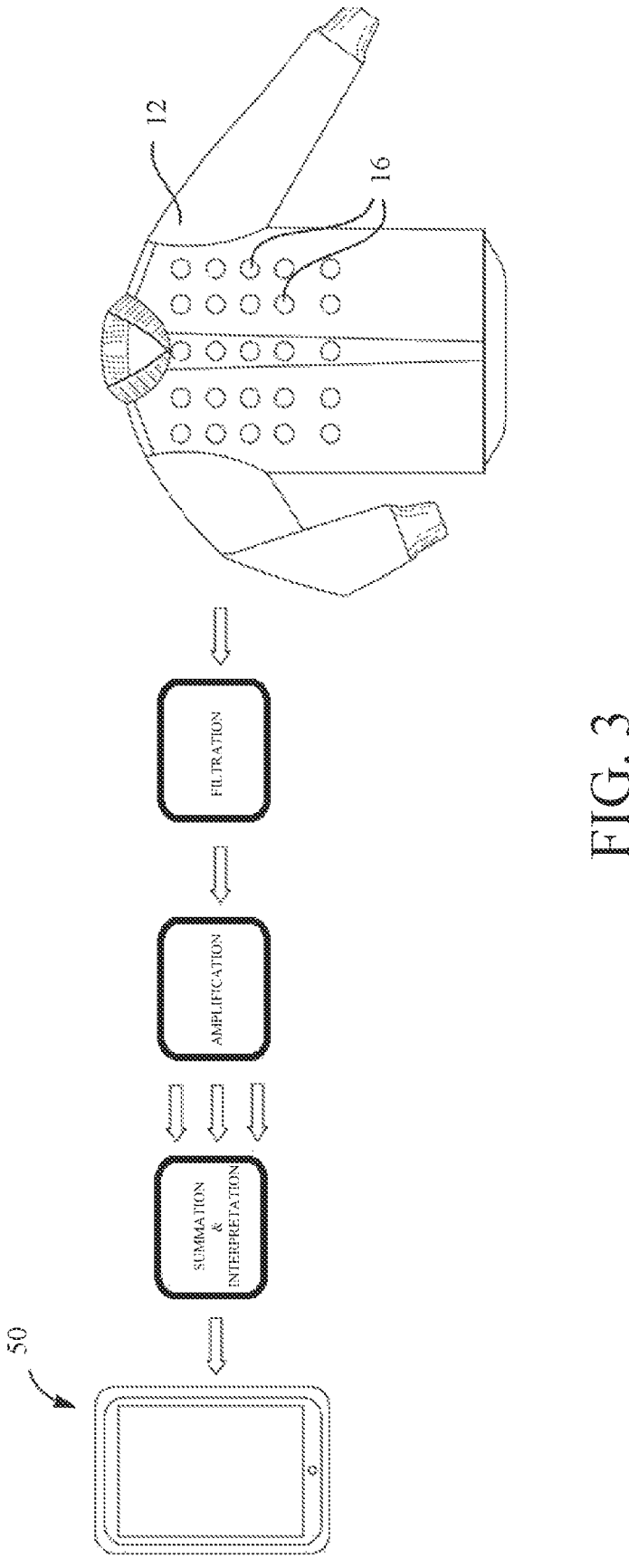
FIG. 3 is a process flowchart illustrating the processing of recorded data from a garment.

As shown in FIG. 3, the microphones 16 may record sounds from the patient's body and communicate those sounds to a computing device 50. While the sounds may be recorded and transmitted directly to the computing device 50 free of manipulation, one or more processes may take place to adjust the sounds recorded prior to a final output of data on the computing device 50 for a medical professional to evaluate. One such process is shown in FIG. 3.

As illustrated, the microphones 16 along the garment 12 may first collect data (e.g., sound) from a patient. The microphones 16 may be site specific such that each data point collected is associated with a specific microphone location, thereby allowing a medical professional to even further pinpoint a targeted medical condition. For example, each microphone 16 may record a site-specific signal so that the plurality of signals recorded by the microphones 16 may be combined to create a sound pulmogram, a sound cardiogram, or both. Once the data is recorded from the microphones 16, the data may then pass through a filtration process. The filtration process may filter out any "white noise" or other extraneous portions of the data recorded by the microphones 16. The filtered data may then pass through an amplification process (if needed) to amplify the sounds recorded by the microphones 16 and place the data in a condition for evaluation. It should be noted that the filtration and amplification of recorded data from the microphones 16 may be completed on each data point from each target specific microphone 16 or may only be completed on a portion of the data points from the microphones 16. After amplification, the data from all of the microphones 16 may be compiled (i.e., summed) in preparation of interpretation. Some or all of the interpretation may be completed by programming on the computing device 50. However, a final output of data on the computing device 50 may still require interpretation or further evaluation from one or more medical professionals.

As may be gleaned from the process above, the garment 12 may compile the data in a beneficial manner such that a medical professional receives a final test result or report for evaluation. For example, the microphones 16 may be provide sufficient data to create a full sound pulmogram, a sound cardiogram, or both. In doing so, the medical professional may also be able to remotely obtain certain patient vitals and create a complete cardiogram of the patient using the medical device system 10. Thus, the medical device system 10 may provide test results sufficient for a medical professional to: evaluate heart sounds of the patient; detect the presence of an issue, including location, strength, type, quality, or a combination thereof of the murmur; a rhythm or the patient's heart; the patient's heart muscle function; or a combination thereof.

Figure 4:
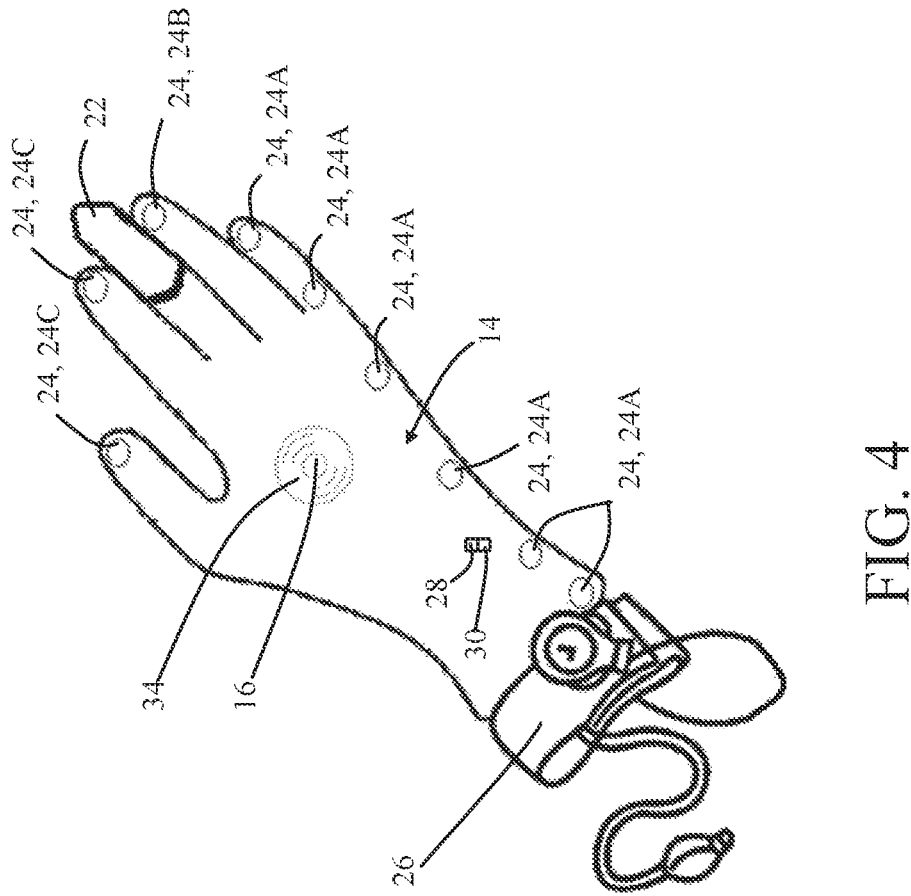
FIG. 4 is a perspective view of a glove of a medical device system.

As shown in FIG. 4, the glove 14 of the medical device system 10 may be used in lieu of the garment 12 described in FIGS. 2 and 3. The glove 14 may also include one or more microphones 16 surrounded by a rubber ear 34 to detect sounds from a patient's body. Additionally, the glove 14 may include a pulse oximeter 22 to determine the patient's oxygen saturation levels. The pulse oximeter 22 may be integrally formed, or connected to, one or more finger holes of the glove 14. To even further check vitals of the patient, the glove 14 may include an integrated blood pressure cuff 26 to check a blood pressure of the patient at a wrist and/or an elbow of the patient. It is envisioned that the glove 14 may include a sleeve such that the blood pressure cuff 26 may be located along the sleeve to more accurately measure blood pressure of a patient near their elbow.

Furthermore, the glove 14 may include a plurality of electrocardiogram leads 24. It is envisioned that the electrocardiogram leads 24 may be positioned along a patient's body in one or more desired positions to record data and create a 12-lead electrocardiogram (EKG). However, it should be noted that the glove 14 may be utilized to record a plurality of data points and create an EKG having greater than 12 leads. For example, a 24-lead EKG recording may be possible by utilizing electrocardiogram leads 24 of the glove 14 for multiple recordings in different locations.

The glove 14 may include, for example, six precordial EKG leads 24A, an aVF EKG lead 24B, and a pair of aVL/aVR EKG leads 24C, that are positioned along the patient in various locations to complete the full 12-lead EKG. These positions are further illustrated in FIGS. 5A-5D below. The data recorded by the glove 14 may then be transmitted by a transmitter 30 of the glove 14 to an external computing device (see FIG. 1). Similarly, the glove 14 may also include a receiver 28 to receive any commands and/or data from an external computing device to configure the glove 14, being testing utilizing the glove 14, or both.

Figure 5A:
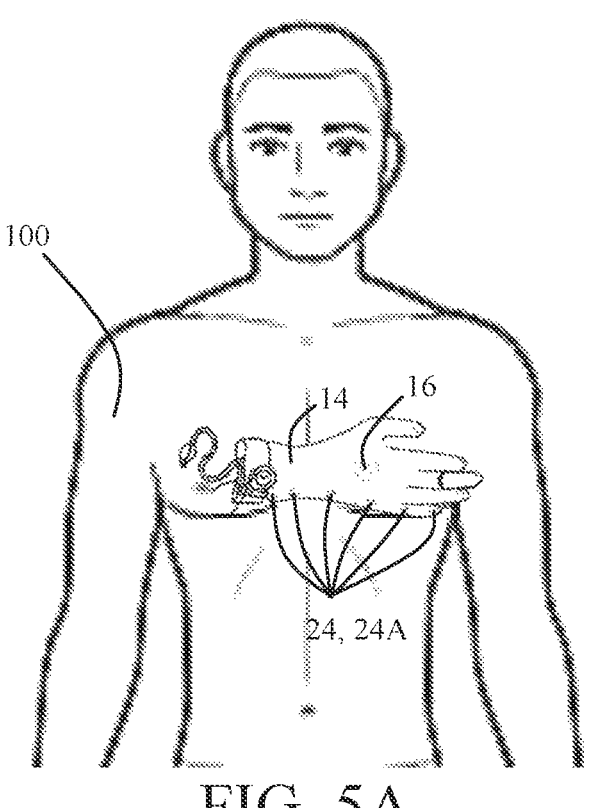
FIG. 5A is a first position of a glove on a user to record precordial electrocardiogram leads of a 12-lead electrocardiogram recording.

A first position of the glove 14 along a user 100 is shown in FIG. 5A. As shown, the glove 14 is held in a substantially horizontal position and pressed against the chest of the user 100. In this position the precordial electrocardiogram leads 24, 24A are recorded. It should be noted that while the precordial EKG leads 24A are recorded in Position A, any of the EKG leads 24 may be recorded in any desired location. Additionally, the microphone 16 may also be utilized in any of the positions described herein to record data within the patient's hand, the patient's chest, or both. Thus, it may be gleaned from the present teachings that in addition to the glove recording data via the electrocardiogram leads 24, the microphone 16 of the glove 14 may beneficially allow a patient to conduct proper auscultation of the heart and/or lungs by positioning the microphone 16 along the chest and/or back over the heart, the lungs, or both.

Figure 5B:
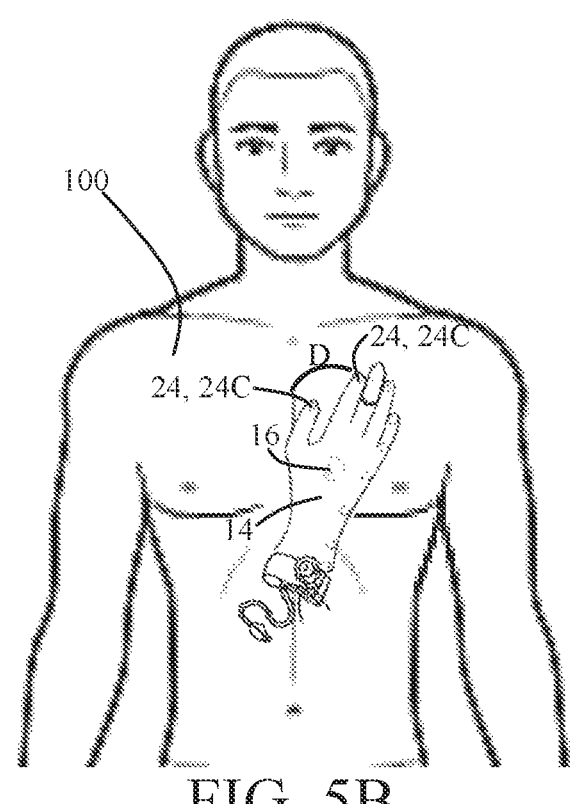
FIG. 5B is a second position of a glove on a user to record aVL and AVR electrocardiogram leads of the 12-lead electrocardiogram recording of FIG. 5A.

As shown in FIG. 5B, after recording the precordial EKG leads 24A, the glove 14 is once again positioned on the patient's chest, but now in a substantially vertical position with the thumb and index finger pointing toward the patient's head. It is envisioned that the thumb and index finger are opened as widely as possible to create a significant distance (D) (e.g., greater than 100 degrees) between the thumb and index finger. As a result, the aVL and aVR EKG leads 24, 24C located on the thumb and index finger may be spaced apart and pressed against the skin of the user 100 on their chest. Thus, the aVR and aVL EKG leads 24, 24C may be recorded.

Figure 5C:
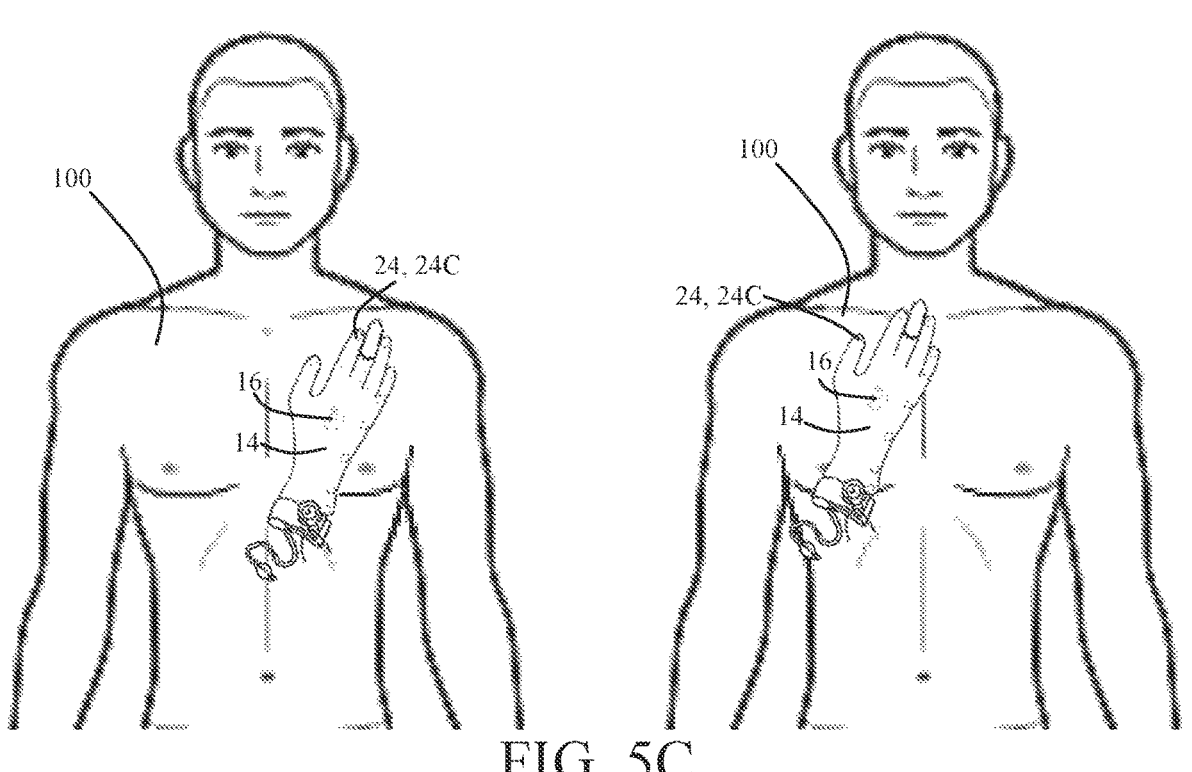
FIG. 5C is a third position of a glove on a user to record aVL and AVR electrocardiogram leads of the 12-lead electrocardiogram recording of FIG. 5A.

However, as shown in FIG. 5C, a second position may be necessary for properly recording the aVR and aVL EKG leads 24, 24C. For example, it is envisioned that some patients may not have adequate spacing between their thumb and index finger to provide a large enough distance (D) between their thumb and index finger. As a result, the recording of the aVR and aVL leads 24, 24C may not be accurate. To combat such an inaccuracy, a user 100 may first record the aVL lead 24, 24C using their index finger. Afterwards, the user 100 may then move the glove 14 and record a proper aVR lead 24, 24C using their thumb. As such, the glove 14 may separately record the aVL and aVR leads 24, 24C in any order and not require simultaneous recordings.

Figure 5D:
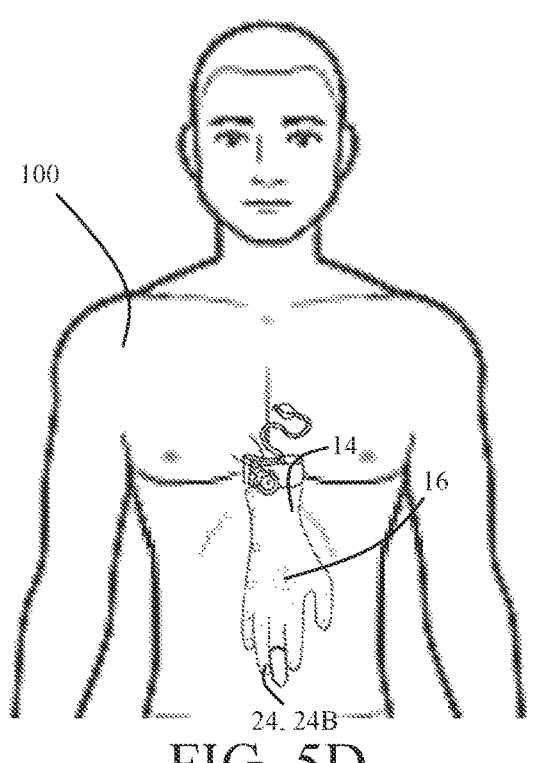
FIG. 5D is a fourth position of a glove on a user to record an aVF electrocardiogram lead of the 12-lead electrocardiogram recording of FIGS. 5A and 5B.

Lastly, as shown in FIG. 5D, after recording of the aVR and aVL EKG leads 24, 24C, the glove 14 may be positioned in a substantially vertical position with the middle finger of the glove 14 positioned downward and pressed against the mid or lower abdomen of the user 100. As a result, the aVF EKG lead 24, 24B located on the middle finger of the glove 14 may be pressed again the mid or lower abdomen of the user 100 to record the aVF EKG lead 24, 24B.

Thus, after completion of the recordings taken in FIGS. 5A-5C, a 12-lead EKG may be compiled. The recordings of the electrocardiogram leads 24 may then be combined with the data recorded by the microphone 16, the pulse oximeter 22, and the blood pressure cuff 26 of the glove 14. This data may then be transmitted from the glove 14 to a computing device for a medical professional to evaluate (see FIG. 1). It should be noted that, like the data recorded using the garment 12 shown in FIG. 3, the data recorded by the glove 14 may be augmented or otherwise manipulated to adjust and/or organize the data recorded. This may include one or more steps or filtration, amplification, or both. Once the data is organized, the external computing device may then generate and display a report for a medical professional to evaluate.

Figure 6:
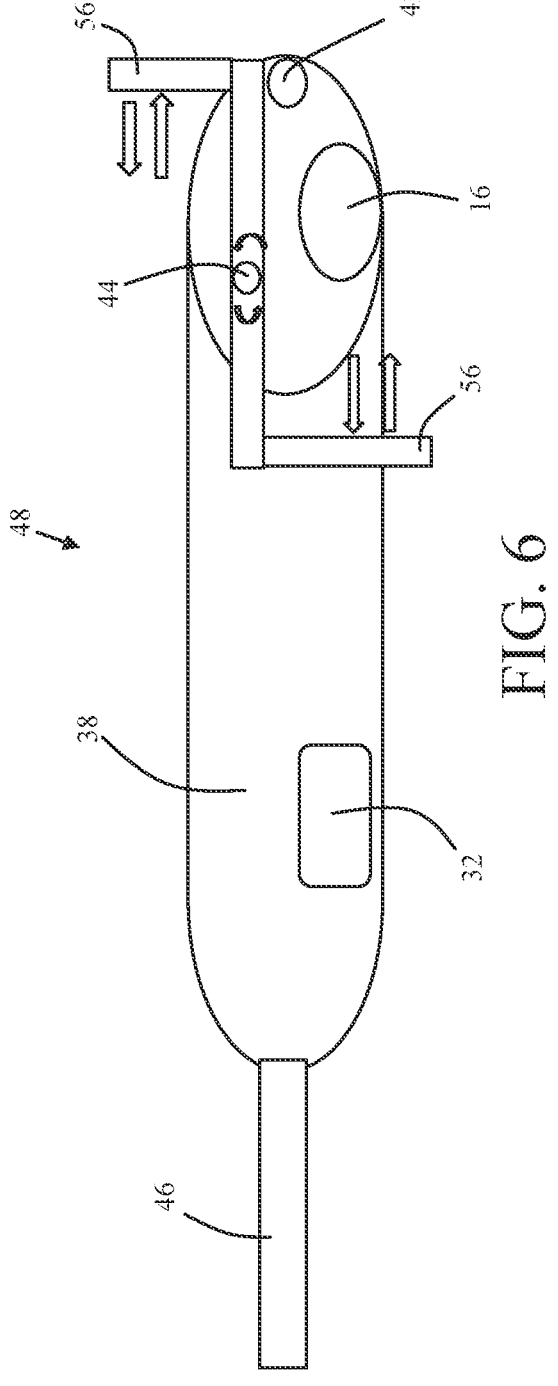
FIG. 6 is a perspective view of a tapping mechanism club in accordance with the present teachings.

FIG. 6 illustrates a perspective of a tapping mechanism that is a club 38 in accordance with the present teachings. It is envisioned that the medical device system described herein may also include the club 38 in addition to the garment, the glove, and/or the chair (see FIG. 1). The club 38 may be used in addition to the garment, the glove, the chair, or a combination thereof within the medical device system to conduct an abdomen examination. However, it should be noted that the club 38 may also be used for further examination of a patient other than an abdomen, such as the heart, lungs, eyes, ears, throat, or a combination thereof. Thus, beneficially, the medical device system may be tailored to a specific patient and may include any number of the devices described herein to evaluate a patient most effectively by providing a plurality of devices to conduct a comprehensive physical examination of the patient.

The club 38 may include a handle 46 to allow for a patient to grasp the club 38 during operation. The handle 46 may extend from a proximal end of the club 38 such that one or more accessories along the club 38 are positioned near an opposing distal end. The club 38 may include a microphone 16 (e.g., a digital stethoscope) to allow a patient to detect and/or record internal sounds from within their own body by positioning the microphone 16 in a desired location. The club 38 may further include a position location sensor 42 disposed along an outer surface of the club 38. The position location sensor 42 may pinpoint a location of potential discomfort for a patient. For example, the club 38 may include a rotary member 44 connected to one or more arms 56 of the tapping mechanism 48, shown as projecting arms. The rotary member 44, whether manually or electronically, may drive a movement of the arms 56 such that the arms 56 tap or otherwise engage a patient's body. As shown, if electronically actuated, the rotary member 44 may be driven by an integrated battery 32 of the club 38. The movement of the arms 56 may be utilized to safely apply pressure to a patient to determine any localized pain along the patient's body. When a location is "tapped" and the patient feels discomfort, the position location sensor 42 may determine a location along the patient's body, thereby more accurately evaluating potential causes of the discomfort. The position location sensor 42 may also be used to establish initial parameters of testing by creating a baseline perimeter along the patient prior to conducting testing. It is envisioned that the 38 may be moved along a patient's body, either by themselves or a third party, to evaluate any and all locations of discomfort in an effective manner.

It should be noted that the club 38 may include any number of arms 56, position location sensors 42, or microphones 16. Additionally, the rotary member 44 may be any actuating member that drives a motion of the arms 56 to "tap" the patient's body. The actuating member may be an electronic actuator or an actuating mechanism that requires manual operation.

While the club 38 may target areas of pain or discomfort of a patient, the club 38 may also be utilized to determine dullness (e.g., the sound resulting from a tapping on a solid organ or mass), rebound tenderness, tympanicity, organomegaly, other potential health concerns, or a combination thereof. For example, the tapping mechanisms 48 may deliver percussion during the "tapping" operation, thereby sending a wave through a location on the patient's body (e.g., the abdomen). That percussion may then be analyzed to interpret tympanicity, dullness, or both. In other words, the club 38 may help a medical professional determine if a part of the patient's body, such as their abdomen, head, chest, back, limbs, or a combination thereof, is soft or hard.

Figure 7:
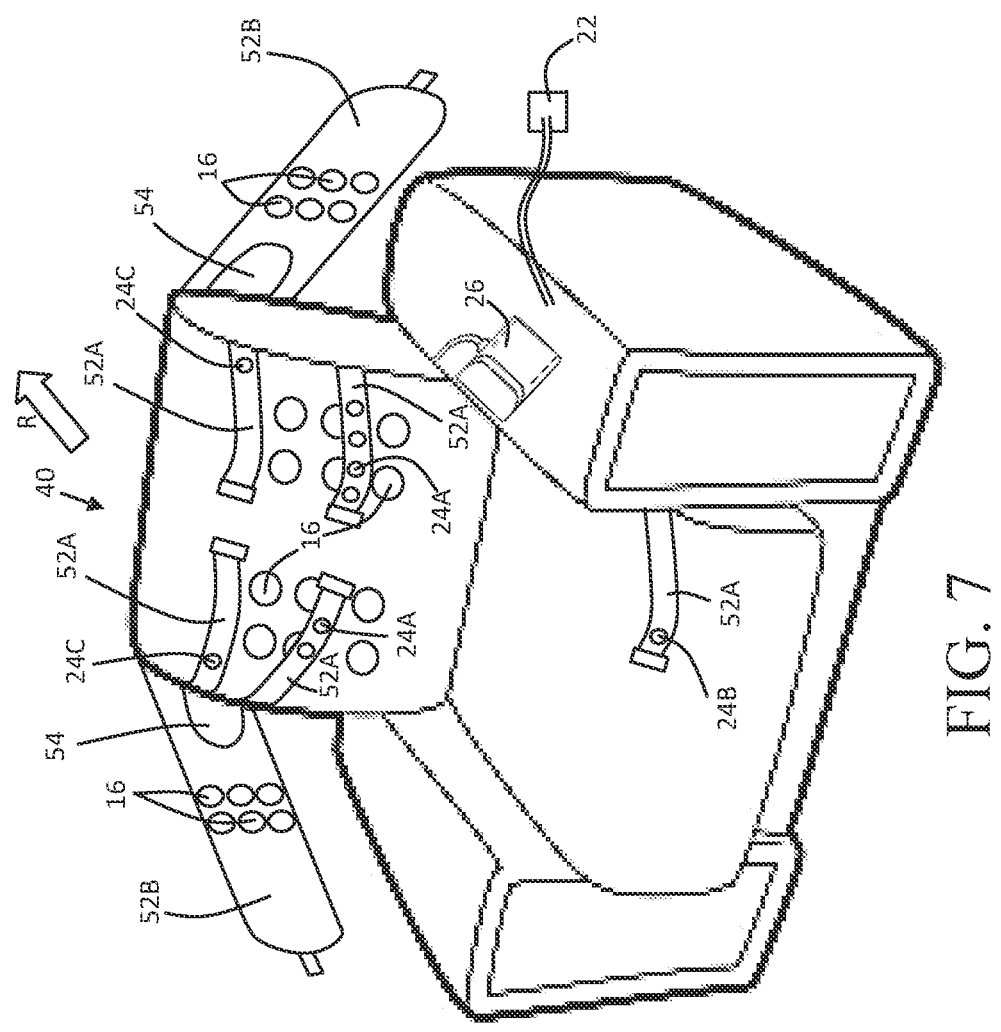
FIG. 7 is a perspective view of a chair of the medical device system.

FIG. 7 is a perspective view of a chair 40 of the medical device system. The chair 40 may be a standard design, size, shape, or a combination thereof. Illustrated in FIG. 7, the chair 40 may be based upon a conventional armchair. The chair 40 may include a plurality of straps 52 that contact a patient's body for collecting data. The straps 52 may include electrocardiogram straps 52A that have a plurality of electrocardiogram leads 24. The electrocardiogram leads 24 may be configured to make direct contact with a patient's skin to conduct an accurate EKG. The electrocardiogram leads 24 may be dispersed along one of the straps 52 or may be disposed on a plurality of straps 52. For example, as shown, upper straps 52A may include the aVL and aVR electrocardiogram leads 24C to contact a patient's upper chest while the additional electrocardiogram straps 52A may include the precordial 24A and aVF 24B electrocardiogram leads. It is envisioned that the electrocardiogram straps 52A may be secured across a patient's torso to directly contact their skin. The electrocardiogram straps 52A may include one or more buckles, clips, fasteners, or a combination thereof to tightly secure the electrocardiogram leads 24 around the patient.

Additionally, the chair 40 may also include microphone straps 52B the tightly secure around the patient by allowing the patient to extend their arms through armholes 54 within the microphone straps 52B. Once the microphone straps 52B are secured using a buckle, clip, fastener, or a combination thereof, a plurality of microphones 16 may be disposed along the patient's chest to detect and/or record internal sounds.

The microphone straps 52B may be secured to the patient while the electrocardiogram straps 52A are free of contact with the patient, or vice versa. However, beneficially, the microphone straps 52B and the electrocardiogram straps 52A may both be secured to the patient to form a multi-layer detection system along the patient. Thus, the chair 40 beneficially records and detects a gamut of data simultaneously while a patient remains seated in a single position.

To further facilitate diagnosis of a patient's potential medical condition, the chair 40 may also include a blood pressure cuff 26, a pulse oximeter 22, or both. These devices 26, 22 may be positioned anywhere along the chair to allow for proper testing. For example, as shown, the blood pressure cuff 26 and the pulse oximeter 22 may both be connected and/or integrated into an arm of the chair 40. Furthermore, the chair may also include one or more microphones 16 (e.g., digital stethoscopes) integrated therein that detect and/or record sound from a patient's back, thereby even further establishing a robust data recording system within the chair 40. Additionally, as shown, the chair 40 may also help facilitate comfort for the patient and accurate testing data by including a reclining feature that allows the chair 40 to recline in a desired direction (R).

Figure 8:
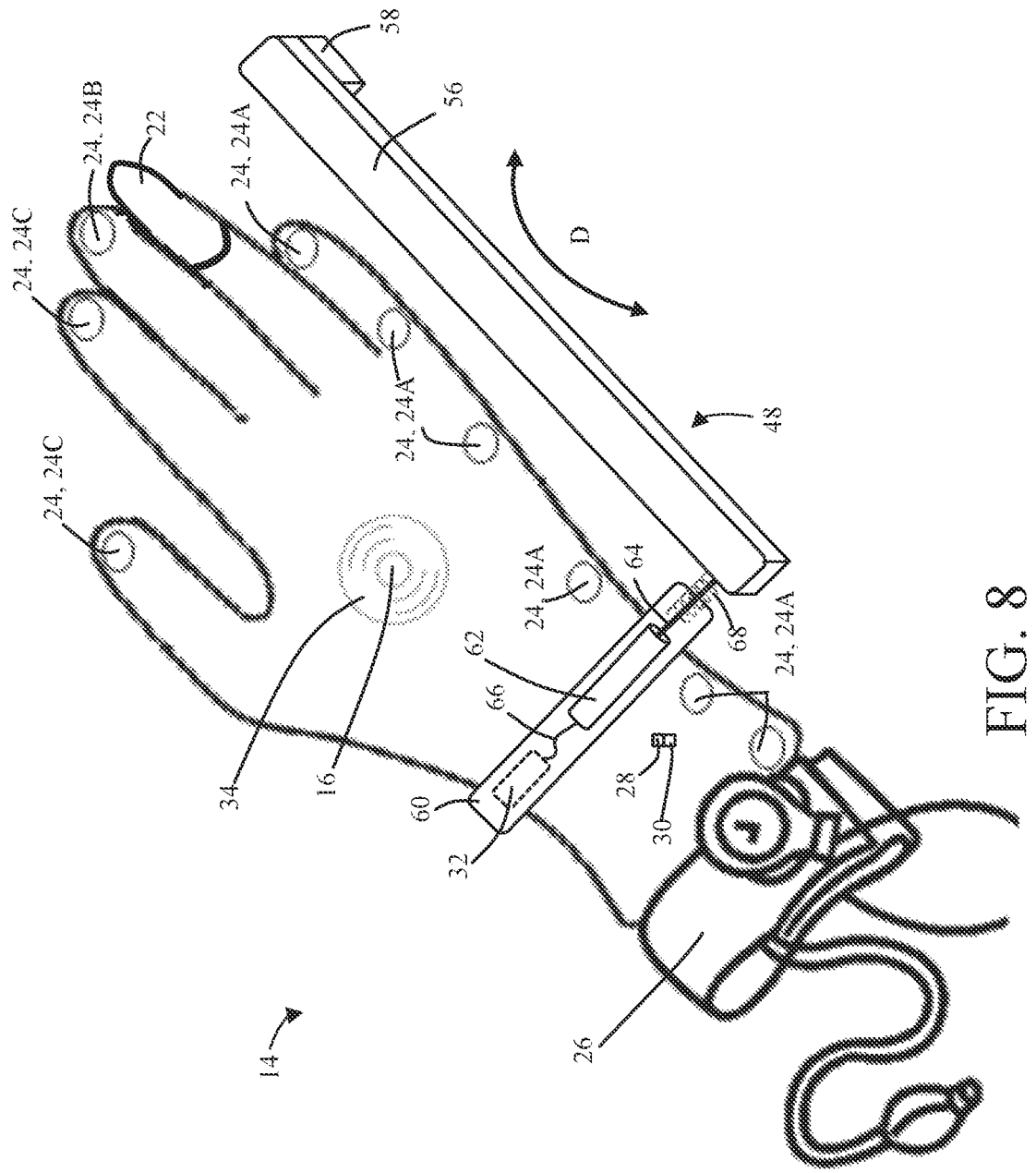
FIG. 8 is a perspective view of a glove of a medical device system having an integrated tapping mechanism in accordance with the present teachings.

FIG. 8 illustrates a perspective view of a glove 14 of a medical device system in accordance with the present teachings. As described above, the glove 14 may include one or more microphones 16 surrounded by a rubber ear 34 to detect sounds from a patient's body. Additionally, the glove 14 may include a pulse oximeter 22 to determine the patient's oxygen saturation levels. The pulse oximeter 22 may be integrally formed, or connected to, one or more finger holes of the glove 14. Furthermore, the glove 14 may include an integrated blood pressure cuff 26 to check the blood pressure of the patient at a wrist and/or an elbow of the patient.

Additionally, as described above, the glove 14 may also include a plurality of electrocardiogram leads 24. It is envisioned that the electrocardiogram leads 24 may be positioned along a patient's body in one or more desired positions to record data and create a 12-lead electrocardiogram (EKG). As shown in FIG. 8, the glove 14 may include six precordial EKG leads 24A, an aVF EKG lead 24B, and a pair of aVL/aVR EKG leads 24C, that are positioned along the glove 14 and adapted to contact a patient in various locations to complete the full 12-lead EKG (see FIGS. 5A-5D).

As discussed above, the medical device system may include a club such as that shown in FIG. 6 for abdomen and chest examination. However, advantageously, it is envisioned that the glove 14 may incorporate its own tapping mechanism 48 to conduct such an abdomen and/or chest examination. As a result, the glove 14 may further integrate various medical devices such that the glove 14 may provide a single adaptive device for conducting a thorough and comprehensive examination for a patient.

As shown in FIG. 8, the tapping mechanism 48 include a housing 60 integrated with, or otherwise connected to, the glove 14. The housing 60 may be a pocket along the glove 14. The housing 60 may also be a separate housing secured to the glove 14 to create a unitary device. For example, the housing 60 may be mounted to the glove using one or more clips, adhesives, other mechanical fasteners, or a combination thereof. As such, the tapping mechanism 48 may in some cases be removed or disconnected from the glove 14 when not in use. For example, the tapping mechanism 48 may be removed during EKG measurements to facilitate proper contact between the glove 14 and a patient.

The housing 60 may contain a motor 62. The motor 62 may be powered by a battery 32 in electrical communication with the motor 62 by wiring 66 (e.g., one or more wires). As such, the battery 32 may be rechargeable, replaceable, or both. Similarly, the present teachings are not particularly limited to any specific type of battery 32. However, it is contemplated that various batteries 32 may be incorporated into the housing 60 to meet packaging constraints, such as a lithium-ion battery, an alkaline battery, a nickel metal hydride (NIMH) battery, or a combination thereof. Similarly, it is envisioned that the motor 62 may be powered by a common power unit of the glove 14. That is, the glove 14 may include a main power source and the motor 62 may be powered by the main power source of the glove 14.

Furthermore, it should be noted that the housing 60 in FIG. 8 has been made transparent for illustrative purposes. However, the housing 60 may include a cover, cap, lid, opening, or a combination thereof to facilitate replacement and/or charging of the battery 32, maintenance of the motor 62, or both. As such, the housing 60 is not limited in size and/or shape based on a given glove 14 structure.

The motor 62 of the tapping mechanism 48 may be in communication with a spindle 64 to articulate the spindle 64. While in certain applications the tapping mechanism 48 may articulate the spindle 64 or other armature in a substantially linear movement, it is envisioned that the motor 62 may translate a rotational movement through the spindle 64 to an arm 56 of the tapping mechanism 48. As a result, as the motor 62 rotationally articulates the spindle 64, the spindle 64 may be in communication with the arm 56 in a manner that translates rotational movement of the spindle 64 into moving the arm 56 in the direction (D). That is, the motor 62 may drive a tapping movement of the arm 56 through the spindle 64 to create a tapping movement of the arm 56 so that the arm 56 may contact a patient.

The tapping movement may be a repetitive motion for tapping. A speed of the tapping movement may be controlled. A direction of the tapping movement may be controlled. Such control may be done by the motor 62 and/or one or more secondary components.

The arm 56 may extend in any manner relative to the glove 14 to facilitate proper contact between the arm 56 and the patient during tapping. As shown, the arm 56 may extend substantially parallel to a length of the glove 14 (i.e., substantially parallel to a longitudinal axis of the glove 14). However, any angle may be formed between the arm 56 of the tapping mechanism 48 and the glove 14. Similarly, the arm 56 may have any desired length to accommodate various patient statures.

Advantageously, due to the configuration of the glove 14, the microphone 16 located along the palm of the glove 14 (e.g., a digital stethoscope) may detect and/or record internal sounds from within a patient's body as a result of the tapping movement and contact between the arm 56 of the tapping mechanism 48 and the patient's body. As a result, a medical expert (e.g., a doctor) may analyze the recordings to diagnose a particular ailment of the patient due to a transmitter 30 located on the glove 14. Moreover, a receiver 28 of the glove 14 may facilitate input from the medical expert into the glove 14 for further customization of the evaluation. Similarly, a corresponding system (e.g., computer application) may compare the recordings with a saved sample to automatically determine certain diagnoses.

Furthermore, it should be mentioned that the arm 56 of the tapping mechanism 48 may also include a pad 58 that makes direct contact with the patient during tapping. The pad may be adhered or otherwise secured to the arm 56 in a manner to contact the patient. That is, the pad 58 may extend along an entire length of the arm 56 on one or more surfaces or the pad 58 may be locally positioned on the arm 56 in a desired location that directly contacts the patient. As a result, the pad 58 may be a compressible or softer material compared to the arm 56 so that contact with the patient does not cause unwanted discomfort. For example, the arm 56 may be substantially rigid compared to the pad 58 (e.g., made of plastic or metal) while the pad 58 may be a rubberized material or a fabric material.

Additionally, the tapping mechanism 48 may include a recoil mechanism 68 in communication with the spindle 64 and/or the arm 56. The recoil mechanism 68 may be positioned within a portion of the arm 56 or substantially around the spindle 64 to decrease overall packaging. The recoil mechanism 68, such as a spring or elastic member, may return the arm 56 to an initial position after the motor 62 drives a tapping movement of the arm 56. For example, the motor 62 may move the arm 56 in a direction towards the patient to contact the patient while the recoil mechanism 68 may move the arm 56 back to its initial position free of contact with the patient.

It should also be noted that while an automatic tapping mechanism 48 has been described above, a mechanical mechanism could also be incorporated into the glove 14. For example, the arms 56 may be spring-loaded and may be manually pulled to load the arm 56 so that release of the arm 56 may result in a tapping movement on a patient.

Based on the above, the tapping mechanism 48 may be utilized to safely apply pressure to a patient to determine any localized pain along the patient's body. When a location is "tapped" and the patient feels discomfort, the glove 14, a medical expert, the patient, or a corresponding computer system may note the location of discomfort for further evaluation. Similarly, the arm 56 and/or the glove 14 may include a position sensor to more accurately determine a location along the patient's body.

Furthermore, while the tapping mechanism 48 may target areas of pain or discomfort of a patient, the tapping mechanism 48 may also be utilized to determine dullness (e.g., the sound resulting from a tapping on a solid organ or mass), rebound tenderness, tympanicity, organomegaly, other potential health concerns, or a combination thereof. For example, the arm 56 may deliver percussion during the "tapping" operation, thereby sending a wave through a location on the patient's body (e.g., the abdomen). That percussion may then be analyzed to interpret tympanicity, dullness, or both. In other words, the tapping mechanism 48 may help a medical professional determine if a part of the patient's body, such as their abdomen, head, chest, back, limbs, or a combination thereof, is soft or hard.

By way of example, a reflected soundwave triggered by the tapping mechanism 48 may be captured by the microphone 16 (e.g., a digital stethoscope) and conveyed to a computer and/or mobile device application. The conveyed data captured by the microphone 16 may then be interpreted and/or analyzed by the application. Such interpretation and analysis by the application may include, but is not limited to, determining locations of dullness and/or tympanicity, determining potential organomegaly (e.g., abnormal enlargement of the liver, spleen, other organs, etc.) and/or internal masses within a person, or a combination thereof.

Additionally, it is envisioned that the percussions created by the tapping mechanism 48 may be utilized for dullness and/or tympanicity mapping. Such mapping may be completed using the tapping mechanism 48 by creating percussions along various locations of a person's body. An associated computer and/or mobile device application may store data based on the various tapping locations to create an overall "map" of a person's body. Such mapping may thus indicate which locations along a person's body may have dullness and/or tympanicity, thereby providing a medical professional an easy reference for diagnosis and further investigation. Rebound tenderness, sound reflection (e.g., dull or tympanic), and localization of such information may provide crucial information for diagnosing a variety of medical concerns, such as issues requiring surgery, bowel concerns based upon oscillation within a person's digestive system, etc. As such, one may glean from the present teachings that the tapping mechanism 48 may beneficially provide a variety of information that may be conveyed or otherwise relayed to an associate computer system for further monitoring and/or analysis.

Figure 9A:
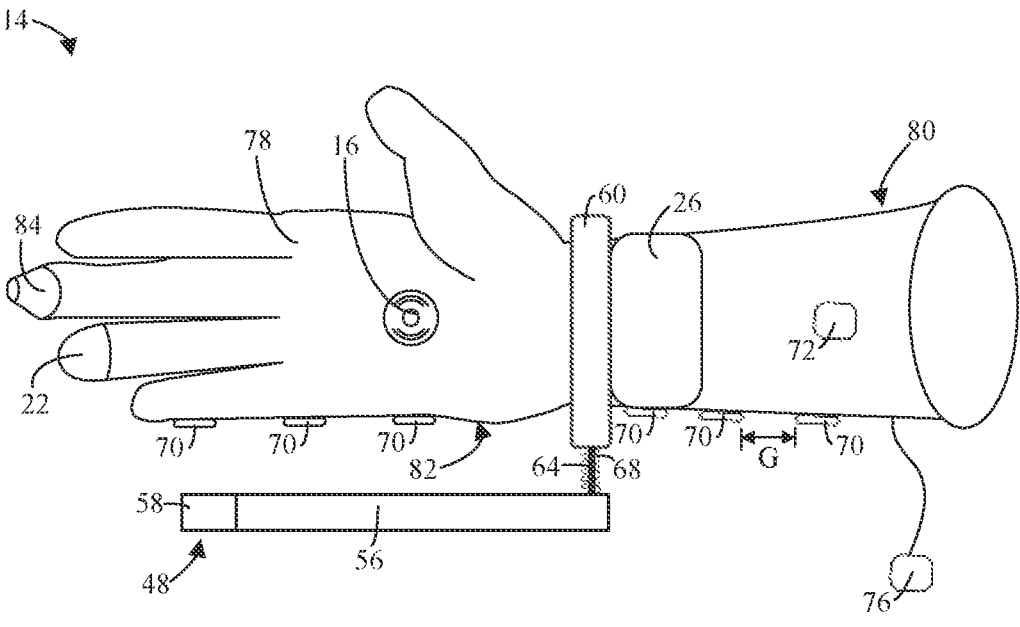
FIG. 9A is a perspective view of a palmar side of a glove in accordance with the present teachings.
Figure 9B:
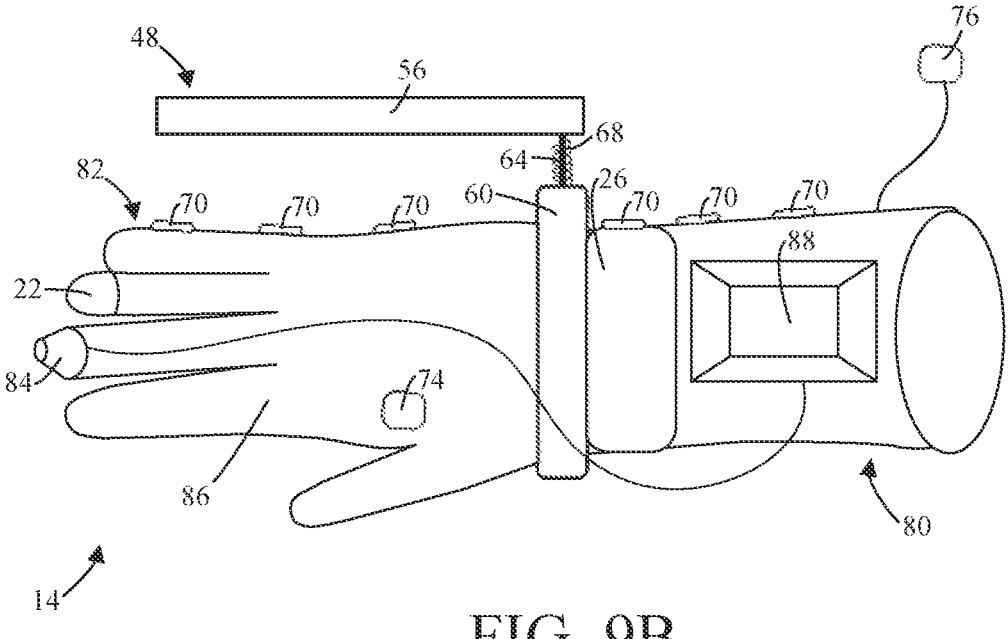
FIG. 9B is a perspective view of a dorsal side of the glove of FIG. 9A.
Figure 9C:
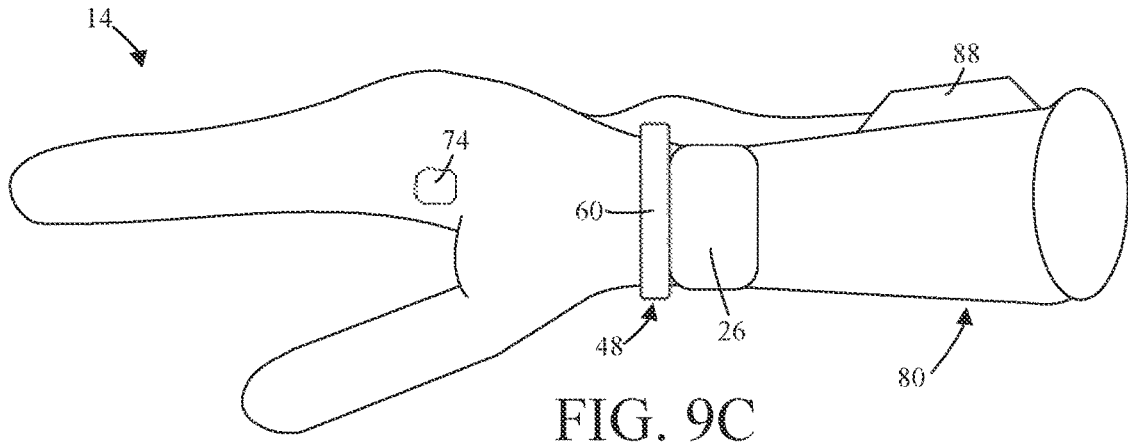
FIG. 9C is a side view of the glove of FIG. 9A.

FIGS. 9A-9C illustrate a glove 14 in accordance with the present teachings. A palmar side 78 of the glove 14 is shown in FIG. 9A and a dorsal side 86 of the glove 14 is shown in FIG. 9B. Additionally, FIG. 9C illustrates a side view of the glove 14.

The glove 14 may include a set of electrocardiogram leads coupled to the glove 14 and configured to record a 12-lead electrocardiogram by contacting a body of a user with the set of electrocardiogram leads. The set of electrocardiogram leads may include one or more precordial leads 70 that are configured to contact a chest of the user. The precordial leads 70 may be positioned along a peripheral edge 82 of the glove 14 the connects the palmar side 78 of the glove 14 to the dorsal side 86 of the glove 14. That is, when the glove 14 is worn by a user to complete a self-medical examination, the precordial leads 70 may be located along and outermost region that may abut a side of the user's hand, whereby the precordial leads 70 may be positioned substantially orthogonal or nonparallel to the palm (i.e., palmar side 78) of the user's hand and the backside (i.e., dorsal side 86) of the user's hand. The precordial leads 70 may extend along the peripheral edge 82 of the glove 14 between a pinkie of the glove 14 and an opening of the glove 14 located at a wrist portion 80 of the glove 14. For example, the peripheral edge 82 of the glove 14 may extend from and/or along a pinkie portion of the glove 14 to a terminal end of the located on the wrist portion 80, whereby the terminal end of the glove 14 may be the opening of the glove 14 in which a user may insert their hand. The peripheral edge 82 may be considered the side edge of the glove 14 from a first end (e.g., tip) of the pinkie portion to an opposing second end of the glove 14 where the opening is located. That is, the peripheral edge 82 may extend along or be substantially parallel to a longitudinal axis of the glove 14.

The precordial leads 70 may be equally spaced from each other and continuously extend along the peripheral edge 82 between the pinkie of the glove 14 and the opening of the glove. A gap (G) between the precordial leads 70 may be uniform or may vary. For example, the precordial leads 70 may include a first set of precordial leads 70 and a second set of precordial leads 70. The first set may be uniformly spaced apart and the second set may be uniformly spaced apart, yet a gap between the first set and the second set may be different than the spacing within the first set and/or the second set. It is envisioned that the precordial leads 70 may be spaced apart in a manner that, when placed against a user's chest transverse to a height of the user, the precordial leads 70 may sufficiently extend across the user's chest to accurately record electrocardiogram measurements. Additionally, the gap (G) between the precordial leads 70 may be large enough to eliminate interference between the precordial leads 70. The gap (G) may be about 1 cm or more, about 2 cm or more, or about 3 cm or more. The gap (G) may be about 6 cm or less, about 5 cm or less, or about 4 cm or less. For example, the gap (G) may be about 3 cm between the precordial leads 70 so that the precordial leads 70 may extend along peripheral edge 82 a total length of about 30 cm or more. The gap (G) between the precordial leads 70 may be dependent on the torso or chest size (e.g., diameter, circumference, etc.) of the user to accommodate various user statures (e.g., adults, children, male, female, etc.).

The precordial leads 70 may coincide with V1-V6 of a conventional precordial electrocardiogram device. That is, the glove 14 may include six precordial leads 70. As a result, the glove 14 may be configured to record the 12-lead electrocardiogram in a single position on the body of the user disposing the precordial leads 70 along the chest of the user. To conduct the 12-lead electrocardiogram in a single position, the glove 14 may also include a right arm lead 72 (e.g., a first arm lead) that is configured to contact a right arm of the user. The right arm lead 72 may be positioned on the palmar side 78 of the glove 14 and may be spaced apart from the peripheral edge 82. The right arm lead 72 may be located within the lining or otherwise extend through a thickness of the glove to contact the right arm. Additionally, the glove 14 may include a left arm lead 74 (e.g., a second arm lead) that is configured to contact the left arm of the user. The left arm lead 74 may be positioned on the dorsal side 86 of the glove 14 and may be spaced apart from the peripheral edge 82. The left arm lead 74 may be positioned on a surface (e.g., an outer surface) of the dorsal side 86 of the glove 14 so that a user may contact the left arm lead 74 with their left arm. Furthermore, the glove 14 may include a leg lead 76 connected to the glove 14 by a wire extending therebetween, whereby the leg lead 76 may be configured to contact a thigh, hip, leg, ankle, left lower abdomen, or a combination thereof of the user. As such, the leg lead 76 may be able to extend from, and be spaced apart from, the glove 14 being worn by the user to reach the thigh, hip, leg, ankle, left lower abdomen, or a combination thereof of the user. Based on the aforementioned leads, the user may conduct a complete 12-lead electrocardiogram recording while maintaining a single position of the leads.

The right arm lead 72 may be positioned on the wrist portion 80 of the glove 14 on the palmar side 78 of the glove 14, whereby the right arm lead 72 may be configured to contact the right arm of the user when the glove is worn on the right hand of the user. The right arm lead 72 may extend through a surface on the palmar side 78 or may located on an interior surface of the palmar side 78 to contact the right arm of the user. For example, the right arm lead 72 may be located on a liner of the glove 14 along an interior surface of the glove 14. The interior surface of the glove 14 may be on the palmar side 78 or the dorsal side 86 of the glove. Additionally, the left arm lead 74 may be positioned on the dorsal side 86 of the glove 14 and may be configured to contact the left arm of the user when the glove 14 is worn on the right hand of the user. For example, the user may extend and position their left arm on top of the left arm lead 74. As such, the left arm lead 74 may be located on an exterior surface of the dorsal side 86 of the glove 14. It should be noted that the left arm lead 74 and the right arm lead 72 may be flipped in certain configurations, such as if a user needed a glove configured for user by the left hand of the user.

As stated above, the right arm lead 72 may be located on the wrist portion 80 of the glove 14. The wrist portion 80 of the glove may extend to or beyond the wrist of the user when the glove 14 is worn by the user. For example, the wrist portion 80 may extend beyond the wrist of the user to a portion of a forearm of the user or may even extend to an elbow of the user. As a result, the right arm lead 72 (e.g., the first lead) may be configured to contact the forearm of the user and provide a more accurate recording for the 12-lead electrocardiogram.

The glove 14 may include one or more additional devices to provide a more comprehensive self-examination, as discussed in further herein. The glove 14 may include a blood pressure cuff 26 coupled to the wrist portion 80 of the glove 14. For example, the blood pressure cuff 26 may be located along the wrist portion 80 in a location that may align with an upper portion of the user's arm to accurately record the user's blood pressure. That is, the wrist portion 80 may be configured to extend to the elbow or even beyond the elbow of the user to align the blood pressure cuff 26 with the upper portion of the user's arm.

The glove 14 may include a camera 84 coupled to a finger of the glove 14. The camera 84 may be coupled to any finger of the glove 14. The camera 84 may be configured to visually inspect and/or record a user's body. That is, the camera 84 may capture and/or transmit images and/or video and an external device, such as those discussed above, for additional evaluation by a medical professional. For example, the camera 84 may be wired or wireless, and the camera 84 may capture and transmit the images and/or video to an external computer in a doctor's office, at which point the doctor may review the images and/or video for medical evaluation. The camera 84 may include one or more interchangeable attachments that facilitate insertion of the camera 84 into orifices of the body of the user, such as the user's ears, nose, and throat. As shown in FIGS. 9A and 9B, the camera 84 may include a conical attachment that allows for deeper insertion in the user's ears, nose, or throat. Such an attachment may be easily disconnected from the camera 84 and may be interchanged with one or more additional attachments. For example, an extendible arm may be attached to the camera 84 to increase the length of the camera 84, a light may be attached to the camera 84, one or more interchangeable lenses may be attached to the camera 84, other structural attachments may be attached to the camera 84, or a combination thereof. The camera 84 may be configured to adjust magnification for capturing and transmitting the images and/or video.

The glove 14 may also include a pulse oximeter 22 located on an additional finger of the glove 14. For example, the pulse oximeter 22 may be located on a first finger of the glove and the camera 84 may located on a second finger of the glove 14. As a result, the pulse oximeter 22 and the camera 84 may be used separately from on another without obstruction. Furthermore, the glove 14 may include a microphone 16 located on the palmar side 78 of the glove and spaced apart from the fingers of the glove 14.

The glove 14 may also include a tapping mechanism 48. The tapping mechanism 48 may be configured to generate a tapping movement that contacts a body of the user to aid in identifying a pain location on the body of the user. As discussed above, the tapping mechanism 48 may be used to identify tympanicity, and/or dullness along the user's body. The tapping mechanism 48 may include a housing 60 coupled to the wrist portion 80 of the glove 14. A motor, such as the motor 62 discussed above, may be disposed in the housing 60. As shown in FIGS. 9A and 9B, the blood pressure cuff 26 may be coupled to the wrist portion 80 and located adjacent to the tapping mechanism 48, such as adjacent to the housing 60 of the tapping mechanism 48. The tapping mechanism 48 may also include an arm 56 that may be in communication with the motor, whereby the motor may articulate the arm 56 to generate the tapping movement that is configured to contact the body of the user. The arm 56 may also include a pad 58 located at or near a distal end of the arm 56 that is configured to contact the user during the tapping movement.

The arm 56 may be coupled to, and spaced apart from, the glove 14. For example, the arm 56 may be coupled to the motor by a spindle 64, and the spindle 64 may be configured to be rotated by the motor to generate the tapping movement. Rotation of the spindle 64 may in turn rotate the arm 56 about an axis of rotation of the spindle 64, thereby generating the tapping movement to contact the body of the user.

Additionally, the tapping mechanism may include a recoil mechanism 68 that is coupled to the arm 56, the spindle 64, or both. The recoil mechanism 68 may be a spring or other biasing member that may be configured to return the arm 56 to an initial position at the tapping movement is generated. For example, the motor may articulate the arm 56 to contact the body of the user with pre-defined force. Once the arm 56 contacts the body of the user, the recoil mechanism 68 may at least in part recoil the arm 56 to return the arm 56 back to its original position.

The set of electrocardiogram leads (e.g., the precordial leads 70, the right arm lead 72, the left arm lead 74, and the leg lead 76), the camera 84, the pulse oximeter 22, the tapping mechanism 48, the blood pressure cuff 26, the microphone 16, or a combination thereof may require an electrical connection to operate. The electrical connection may be wired or wireless. The electrical connection may connect the aforementioned devices with an electrical device 88.

The electrical device 88 may be coupled to the wrist portion 80 of the glove 14 and may be configured to communicate with the set of electrocardiogram leads, the tapping mechanism 48, the pulse oximeter 22, the camera 84, the blood pressure cuff 26, the microphone 16, or a combination thereof. As stated above, the devices may be in wired or wireless communication with the electrical device 88. The electrical device 88 may include a power source, such as a battery, that may be configured to power the set of electrocardiogram leads, the tapping mechanism 48, the pulse oximeter 22, the camera 84, the blood pressure cuff 26, the microphone 16, or a combination thereof. As a result, the glove 14 may facilitate an overall wireless self-medical examination device, whereby the glove 14 may not require a wired connection to an external power source, such as a wall outlet. Additionally, it should be noted that the electrical device 88 may include one or more internal electrical components configured to transmit and/or receive data from the aforementioned devices of the glove 14, manipulate the data from the aforementioned devices of the glove 14, or both. For example, the electrical device 88 may include a controller, a printed circuit board (PCB), a memory storage unit, or a combination thereof.

Figure 10:
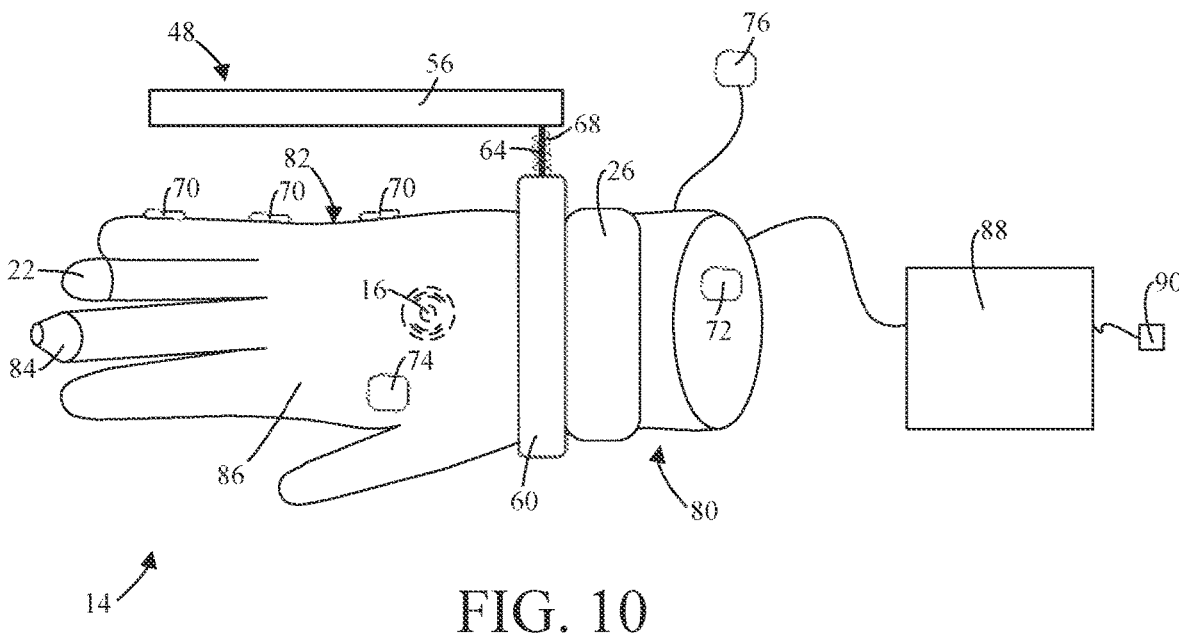
FIG. 10 is a perspective view of a dorsal side of a glove in accordance with the present teachings.

FIG. 10 illustrates a dorsal side of a glove 14. The glove 14 may be similar to the glove 14 discussed in FIG. 9. The glove 14 may include a set of electrocardiogram leads configured to record a 12-lead electrocardiogram. As discussed above, the set of electrocardiogram leads may include precordial leads 70 disposed along a peripheral edge 82 of the glove 14, a right arm lead 72 disposed in a wrist portion 80 of the glove, a left arm lead 74 disposed on the dorsal side 86 of the glove 14, and a leg lead 76 connected to the glove 14 by a wire.

While the glove 14 in FIG. 9 includes six precordial leads 70, the glove 14 shown in FIG. 10 may include three precordial leads 70. As discussed in further detail below, this may facilitate taking a 12-lead electrocardiogram based on a first and a second recording position along the body of the user. Additionally, the wrist portion 80 of the glove 14 may be shorted so that the wrist portion 80 may extend to or near the wrist of the user's arm when the glove 14 is worn by the user.

The glove 14 may also include a camera 84, a pulse oximeter 22, a blood pressure cuff 26, and a microphone 16. The camera 84, the pulse oximeter 22, the blood pressure cuff 26, and the microphone 16 may be positioned and may operate as discussed above. Additionally, the glove 14 may include a tapping mechanism 48. As discussed above, the tapping mechanism 48 may include a housing 60 coupled to the glove 14. The housing 60 may contain a motor that is configured to articulate an arm 56 via a spindle 64 disposed therebetween. The tapping mechanism 48 may also include a recoil mechanism 68 coupled to the arm 56, the spindle 64, the housing 60, or a combination thereof to return the arm 56 back to its original position after a tapping movement is generated by the motor.

One or more of the devices of the glove 14 may be in communication with an electrical device 88 that may include a power source. The electrical device 88 may be in wired or wireless communication with the devices of the glove 14. For example, the electrical device 88 may be wired to the glove 14 and spaced apart from the glove 14 to provide a more compact and lightweight glove. Additionally, the electrical device 88 may include or be connected to an output 90, whereby the output 90 may be configured to connect the electrical device 88—and thus the glove 14—to an external device, such as a computing device, an external power source (e.g., wall outlet), etc.

Figure 11:
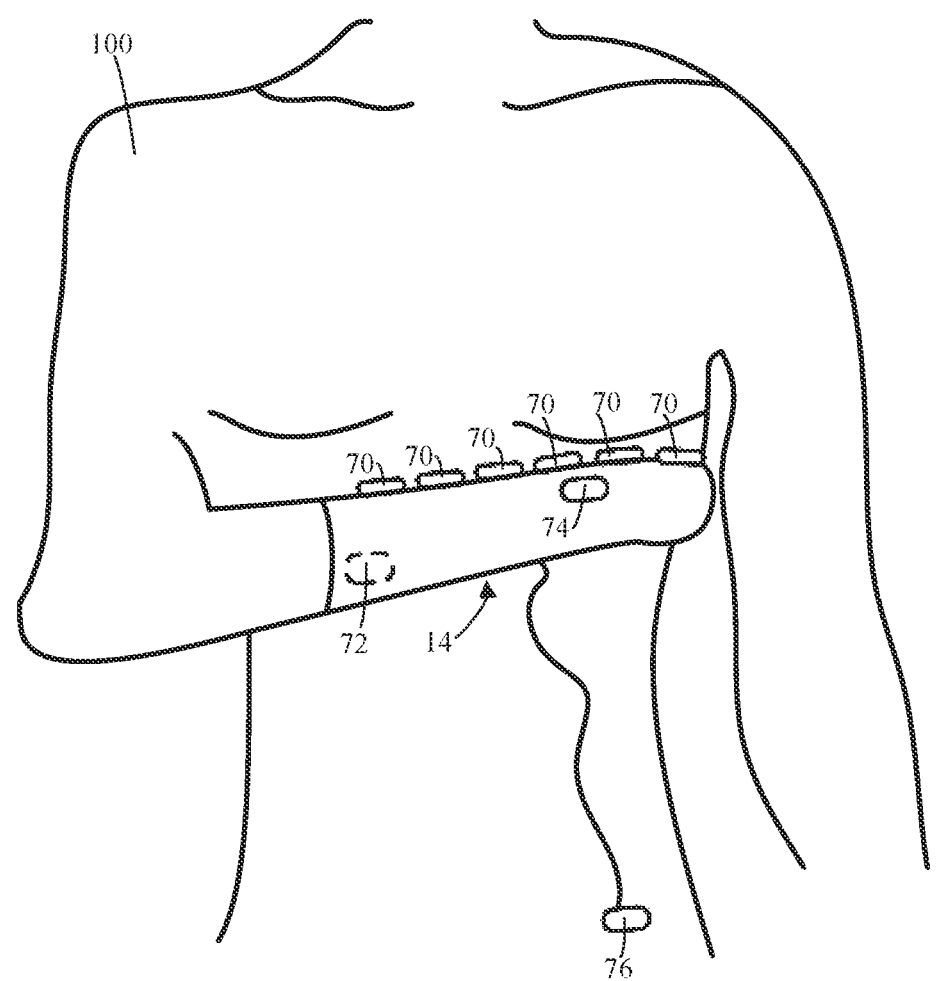
FIG. 11 illustrates positioning of the glove of FIGS. 9A-9C on a user to conduct a 12-lead electrocardiogram recording.

FIG. 11 illustrates positioning of the glove 14 shown in FIGS. 9A-9C on a user 100 (e.g., a patient). As discussed above, the glove 14 may include six precordial leads 70, a right arm lead 72, a left arm lead 74, and a leg lead 76. The glove 14 may be configured to record a 12-lead electrocardiogram in a single position on the body of the user 100, such as the position shown in FIG. 11, with simultaneous acquisition of data from all the aforementioned leads to produce a 12-lead electrocardiogram.

The glove 14 may be configured to record the 12-lead electrocardiogram by disposing the precordial leads 70 along the chest of the user 100 in a direction substantially transverse to a height (e.g., a longitudinal access) of the user 100 so that the precordial leads 70 may extend along substantially all of the chest of the user 100. As discussed above, the precordial leads 70 may be located on a peripheral edge of the glove 14. As a result, the user 100 may wear the glove 14 on their right hand and/or arm and contact the peripheral edge of the glove 14, including the precordial leads 70, to the chest. Additionally, the right arm lead 72 (e.g., the first arm lead) may contact the right arm (e.g., the first arm) of the user. For example, the right arm lead 72 may contact the forearm of the user. Furthermore, the left arm lead 74 (e.g., the second arm lead) may be located on a dorsal side of the glove 14 so that, when the precordial leads 70 contact the chest of the user 100, the left arm lead 74 may be exposed and free of contact with the body of the user. The user 100 may then move their left arm (e.g., their second arm) and rest it on top of the left arm lead 74. Such movement of the left arm is not shown in FIG. 11 for illustrative purposes only. Moreover, the leg lead 76 may extend from the glove 14 and may be placed in a manner that contacts a leg, hip, or ankle of the user. The leg lead 76 may be wired to the glove 14 or may have a wireless connection with the glove 14. As a result of the above contact points in the position shown in FIG. 11 and discussed above, the 12-lead electrocardiogram may be successfully and accurately recorded.

Figure 12A:
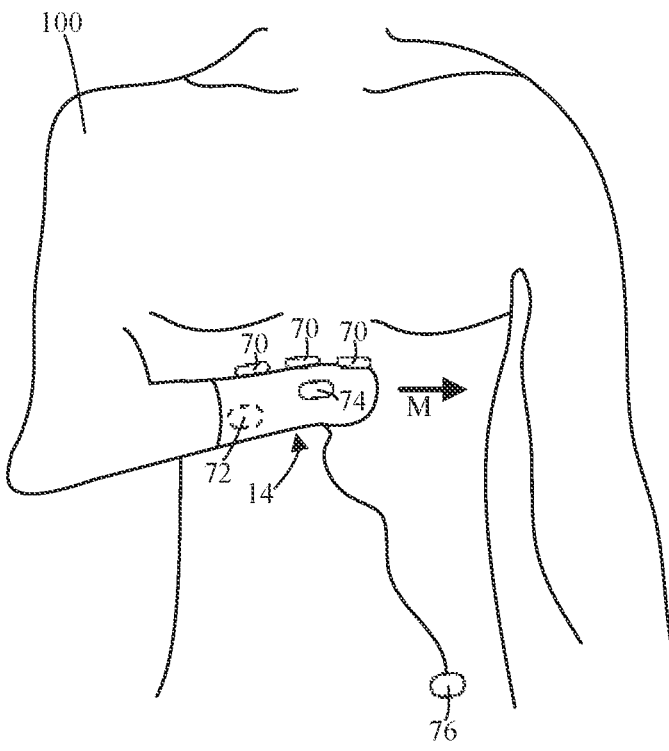
FIG. 12A illustrates a first position of the glove of FIG. 10 on a user to conduct a recording of a first portion of a 12-lead electrocardiogram.
Figure 12B:
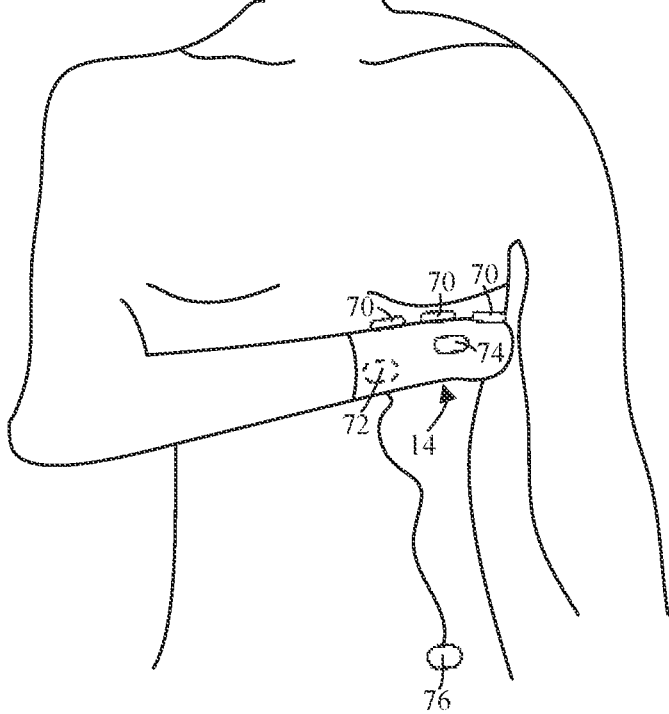
FIG. 12B illustrates a second position of the glove of FIG. 10 on a user to conduct a recording of a second portion of a 12-lead electrocardiogram.

FIGS. 12A and 12B illustrate position of the glove 14 shown in FIG. 10 on a user 100 (e.g., a patient). As discussed above, the glove 14 may include three precordial leads 70, a right arm lead 72, a left arm lead 74, and a leg lead 76. The glove 14 may be configured to record a 12-lead electrocardiogram using the set of electrocardiogram leads. The glove 14 may record the 12-lead electrocardiogram using a first position, as shown in FIG. 12A, and a second position, as shown in FIG. 12B.

The glove 14 may be configured to record a first portion of the 12-lead electrocardiogram using the precordial leads 70 in the first position by contact the precordial leads 70 to the chest of the user near and/or slight right of the longitudinal axis of the user 100 along their chest. The precordial leads 70 may be positioned substantially transverse to the longitudinal axis (e.g., the axis to measure a height of the user 100) along the chest of the user 100. After recording of the first portion of the 12-lead electrocardiogram in the first position, the glove may be moved in the direction (M) to the second position. The glove 14 may then be configured to record a second portion of the 12-lead electrocardiogram using the precordial leads 70 in the second position on the cheat of the user 100. As shown in FIGS. 12A and 12B, the second position on the body of the user may be different than the first position, whereby the precordial leads 70 may be positioned along the chest of the user 100 transverse to the longitudinal axis of the user 100 and along a left side of the chest.

Additionally, in the first position and/or the second position, the right arm lead 72 may contact the right arm of the user 100 for recording. Furthermore, similar to the positioning discussed in FIG. 10, the left arm may be folded onto the left arm lead 74 for recording. Lastly, the leg lead 76 may be positioned to contact the hip, leg, or ankle of the user 100. It should be noted that recordings by the right arm lead 72, the left arm lead 74, and the leg lead 76 may be completed in the same position or different positions. For example, recordings by the right arm lead 72, the left arm lead 74, and the leg lead 76 may all be completed in the second position shown in FIG. 12B. Once the first portion and the second portion are recorded, the first portion and the second portion may together create a complete 12-lead electrocardiogram recording.

The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the specific embodiments of the present invention as set forth are not intended as being exhaustive or limiting of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps.

The disclosure of "a" or "one" to describe an element or step is not intended to foreclose additional elements or steps.

While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Unless otherwise stated, a teaching with the term "about" or "approximately" in combination with a numerical amount encompasses a teaching of the recited amount, as well as approximations of that recited amount. By way of example, a teaching of "about 100" encompasses a teaching of 100+/−15.

The disclosures of all articles and references, including patent applications and publications, are incorporated by reference in their entirety for all purposes. Other combinations are also possible as will be gleaned from the following claims, which are also hereby incorporated by reference into this written description in their entirety.

What is claimed is:

1. A glove comprising:
a set of electrocardiogram leads coupled to the glove and configured to record a 12-lead electrocardiogram by contacting a body of a user with the set of electrocardiogram leads, the set of electrocardiogram leads including:
precordial leads (V1-V6) configured to contact a chest of the user and positioned along a peripheral edge of the glove,
a first arm lead (aVR) configured to contact a first arm of the user and positioned on an interior surface of a palmar side or a dorsal side of the glove spaced apart from the peripheral edge, and
a second arm lead (aVL) configured to contact a second arm of the user and positioned on the dorsal side of the glove spaced apart from the peripheral edge and configured to record an electrocardiogram when the dorsal side of the glove contacts the second arm of the user, wherein the peripheral edge connects the palmar side of the glove and the dorsal side of the glove at an outermost region that is configured to abut a side of a hand of the user;
a tapping mechanism configured to generate a tapping movement that contacts a body of the user to aid in identifying a pain location on the body of the user; and
an acoustic sensor device configured to record sounds from within the body of the user as a result of the tapping movement of the tapping mechanism.

2. The glove of claim 1, wherein the precordial leads (V1-V6) extend along the peripheral edge of the glove between a pinkie of the glove and an opening located at a wrist portion of the glove.

3. The glove of claim 2, wherein the precordial leads (V1-V6) are equally spaced from each other and continu-ously extend along the peripheral edge between the pinkie of the glove and the opening of the glove.

4. The glove of claim 1, wherein the glove includes three precordial leads, the glove is configured to record a first portion of the 12-lead electrocardiogram using the precordial leads (V1-V6) in a first position on the body of the user, the glove is configured to record a second portion of the 12-lead electrocardiogram using the precordial leads (V1-V6) in a second position on the body of the user that is different than the first position, and the first portion and the second portion together create a complete 12-lead electrocardiogram recording.

5. The glove of claim 1, wherein the glove includes six precordial leads (V1-V6), and the glove is configured to record the 12-lead electrocardiogram in a single position on the body of the user by:
disposing the precordial leads (V1-V6) along a chest of the user;
contacting the first arm lead (aVR) to the first arm of the user;
contacting the second arm lead (aVL) to the second arm of the user; and
contacting a leg lead (aVF) of the set of electrocardiogram leads to a leg of the user.

6. The glove of claim 1, wherein the glove further comprises a leg lead (aVF) connected to the glove by a wire or a wireless connection, and wherein the leg lead is configured to contact a leg of the user.

7. The glove of claim 6, wherein the glove further comprises a blood pressure cuff coupled to a wrist portion of the glove.

8. The glove of claim 7, wherein the glove further comprises a tapping mechanism that includes:
a housing coupled to the wrist portion of the glove;
a motor disposed in the housing; and
an arm in communication with the motor, wherein the motor articulates the arm to generate a tapping movement that is configured to contact the body of the user.

9. The glove of claim 8, wherein the arm is coupled to the motor by a spindle, and the spindle is configured to be rotated by the motor to generate the tapping movement.

10. The glove of claim 9, wherein the glove further comprises a camera coupled to a finger of the glove, and wherein the camera includes one or more interchangeable attachments that facilitate capturing images of an ear, an eye, skin, an oral cavity, other visual abnormalities, or any combination thereof of the user.

11. A glove comprising:
a set of electrocardiogram leads (V1-V6) coupled to the glove and configured to record an electrocardiogram of a user, the set of electrocardiogram leads including:
three or six precordial leads (V1-V6) that extend along a peripheral edge of the glove that connects a palmar side of the glove to a dorsal side of the glove,
a right arm lead (aVR) positioned embedded on a wrist portion of the glove in a liner of the glove on the palmar side of the glove, wherein the right arm lead is configured to contact a right arm of the user when the glove is worn on a right hand of the user,
a left arm lead (aVL) positioned on an outer surface of the dorsal side of the glove that is configured to contact a left arm of the user when the glove is worn on the right hand of the user, and
a leg lead connected to the glove by a wire, wherein the peripheral edge extends parallel to a longitudinal axis of the glove;

a tapping mechanism that includes:

a housing coupled to the wrist portion of the glove, a motor disposed in the housing, and an arm in communication with the motor, wherein the motor articulates the arm to generate a tapping movement that is configured to contact a body of the user;

a pulse oximeter located on a first finger of the glove;

a camera located on a second finger of the glove;

a blood pressure cuff coupled to the wrist portion and located adjacent to the tapping mechanism; and an acoustic sensor device configured to record sounds from within the body of the user as a result of the tapping movement of the tapping mechanism.

12. The glove of claim 11, wherein the set of electrocardiogram leads are configured to record a 12-lead electrocardiogram.

13. The glove of claim 11, wherein the glove further comprises an electrical device coupled to the wrist portion of the glove that is configured to communicate with the set of electrocardiogram leads, the tapping mechanism, the pulse oximeter, the camera, the blood pressure cuff, or a combination thereof.

14. The glove of claim 13, wherein the electrical device includes a power source that is configured to power the set of electrocardiogram leads, the tapping mechanism, the pulse oximeter, the camera, the blood pressure cuff, the acoustic sensor device, or a combination thereof.

15. The glove of claim 12, wherein the glove is configured to be worn by the user to conduct a self-examination using the set of electrocardiogram leads, the tapping mechanism, the pulse oximeter, the camera, the blood pressure cuff, the acoustic sensor device, or a combination thereof.

16. A glove comprising:

a set of electrocardiogram leads configured to record a 12-lead electrocardiogram of a user that are coupled to the glove and disposed on a dorsal side of the glove, a palmar side of the glove, and a peripheral edge of the glove that connects the palmar side to the dorsal side, wherein the peripheral edge extends parallel to a longitudinal axis of the glove;

a tapping mechanism configured to generate a tapping movement that contacts a body of the user to aid in identifying a pain location on the body of the user; and an acoustic sensor device configured to record internal sounds from within the body of the user as a result of the tapping movement of the tapping mechanism.

17. The glove of claim 16, wherein a power source is coupled to the glove and configured to power the set of electrocardiogram leads, the tapping mechanism, or both.

18. The glove of claim 16, wherein the tapping mechanism includes an arm coupled to, and spaced apart from, the glove, and wherein the arm is configured generate the tapping movement.

19. The glove of claim 18, wherein a motor of the tapping mechanism articulates the arm to generate the tapping movement.

20. The glove of claim 18, wherein the tapping mechanism includes a recoil mechanism that is coupled to the arm and configured to return the arm to an initial position after the tapping movement is generated.

* * * * *